US009445761B2

(12) United States Patent
Klein et al.

(10) Patent No.: US 9,445,761 B2
(45) Date of Patent: Sep. 20, 2016

(54) LANCET EJECTION AND ADVANCEMENT MECHANISM FOR MULTI-LANCET CARTRIDGE

(71) Applicant: FACET TECHNOLOGIES, LLC, Kennesaw, GA (US)

(72) Inventors: Benjamin L. Klein, Gainesville, GA (US); Lauren R. Pusey, Woodstock, GA (US)

(73) Assignee: FACET TECHNOLOGIES, LLC, Atlanta, GA (US)

( * ) Notice: Subject to any disclaimer, the term of this patent is extended or adjusted under 35 U.S.C. 154(b) by 258 days.

(21) Appl. No.: 14/325,650

(22) Filed: Jul. 8, 2014

(65) Prior Publication Data

US 2015/0012026 A1    Jan. 8, 2015

Related U.S. Application Data

(60) Provisional application No. 61/843,711, filed on Jul. 8, 2013.

(51) Int. Cl.
*A61B 5/151* (2006.01)
*A61B 5/15* (2006.01)

(52) U.S. Cl.
CPC .............. *A61B 5/151* (2013.01); *A61B 5/1411* (2013.01); *A61B 5/150022* (2013.01);
(Continued)

(58) Field of Classification Search
CPC ................ A61B 5/1411; A61B 5/151; A61B 5/15115–5/15117; A61B 5/15146–5/15174; A61B 5/15126–5/15132
See application file for complete search history.

(56) References Cited

U.S. PATENT DOCUMENTS 7,077,828 B2    7/2006  Kuhr et al.
2006/0173478 A1*  8/2006  Schraga ............... A61B 5/1411
606/181

(Continued)

FOREIGN PATENT DOCUMENTS

FR          2797579 A1    2/2001
JP          200546474 A   2/2005
WO          2006083676 A2  8/2006

OTHER PUBLICATIONS

International Search Report and Written Opinion for PCT/US2014/045686; Sep. 2, 2014; 10 pgs.

*Primary Examiner* — Julian W Woo
*Assistant Examiner* — Shaun L David
(74) *Attorney, Agent, or Firm* — Gardner Groff Greenwald & Villanueva, PC

(57) ABSTRACT

A lancing device includes an advance-and-eject mechanism with a positioning member for manipulating a series of interconnected lancets. The advance-and-eject mechanism includes an actuator, a control channel, a cam-and-follower mechanism, one or more axial-contact members, and one or more angular-contact members. Actuating the actuator relative to the control channel imparts rotational and axial forces on the positioning member, and the cam-and-follower mechanism selectively restricts rotational and/or axial motion of the positioning member to induce first-stage rotation, second-stage translation, third-stage rotation, and fourth-stage translation. The first-stage rotation rotates the axial-contact members into an interference position, the second-stage translation advances the axial-contact members and the lancet, the third-stage rotation rotates the angular-contact members and the lancet to sever its rearside connection, and the fourth-stage translation advances the axial-contact members and the lancet to a position free of the serial-interconnected lancets thereby ejecting it from the lancing device.

20 Claims, 16 Drawing Sheets

(52) U.S. Cl.
CPC ...... *A61B 5/15107* (2013.01); *A61B 5/15117* (2013.01); *A61B 5/15128* (2013.01); *A61B 5/15155* (2013.01); *A61B 5/15174* (2013.01); *A61B 5/150259* (2013.01); *A61B 5/150412* (2013.01)

(56) References Cited

U.S. PATENT DOCUMENTS

| | | | | |
|---|---|---|---|---|
| 2006/0229652 A1* | 10/2006 | Iio | ........................ | A61B 5/1411 606/182 |
| 2007/0083222 A1 | 4/2007 | Schraga | | |
| 2007/0233167 A1* | 10/2007 | Weiss | .................... | A61B 5/1411 606/182 |
| 2009/0125048 A1* | 5/2009 | Robbins | ............... | A61B 5/1411 606/182 |
| 2011/0040317 A1* | 2/2011 | Lee | ...................... | A61B 5/1411 606/182 |
| 2011/0060292 A1 | 3/2011 | Schraga | | |
| 2011/0092855 A1* | 4/2011 | List | ...................... | A61B 5/1411 600/583 |
| 2011/0160759 A1* | 6/2011 | Schraga | ............... | A61B 5/1411 606/172 |
| 2013/0158586 A1* | 6/2013 | Pusey | .................. | A61B 5/1411 606/173 |
| 2014/0074138 A1* | 3/2014 | Kan | ................... | A61B 5/15117 606/182 |

\* cited by examiner

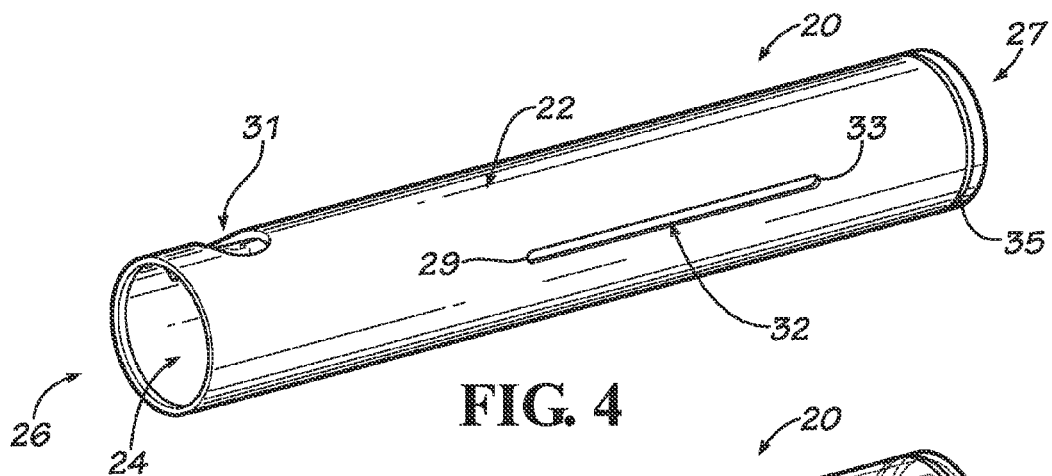
FIG. 4
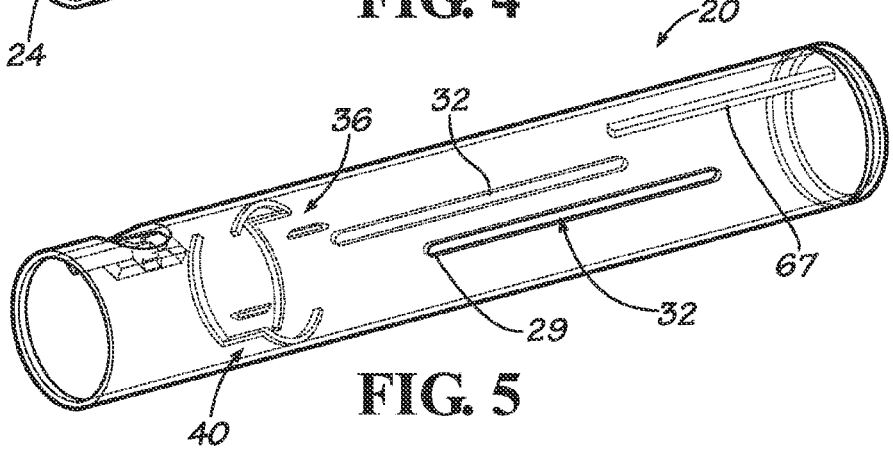
FIG. 5
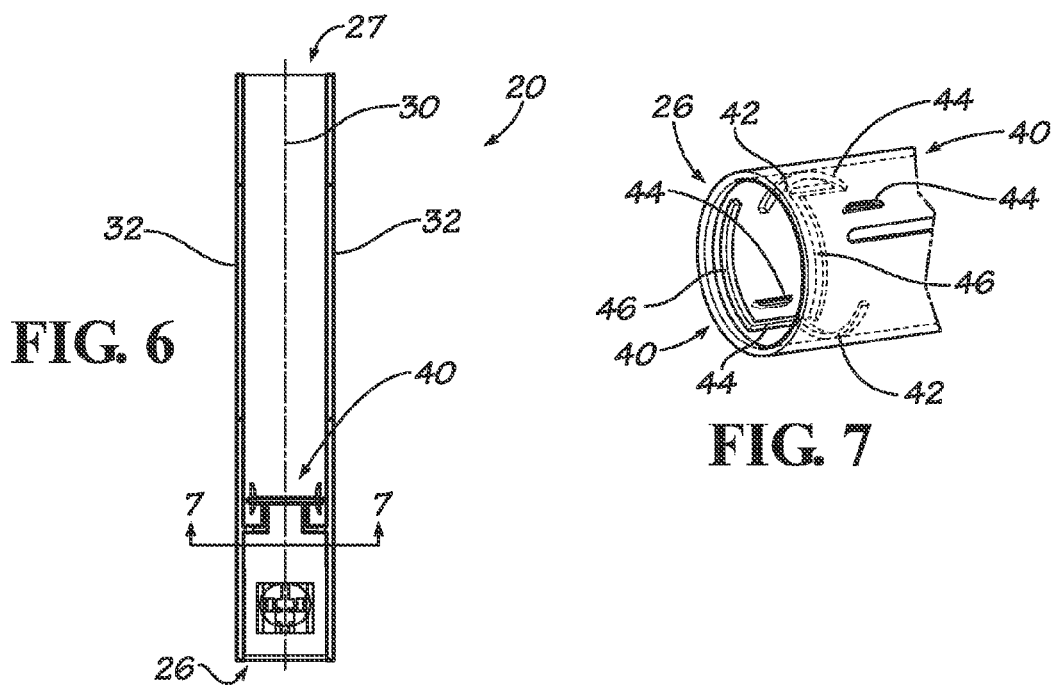
FIG. 6
FIG. 7

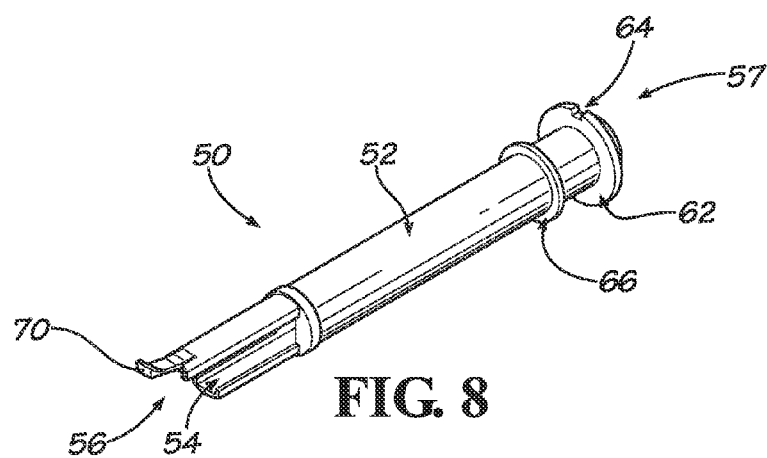
FIG. 8
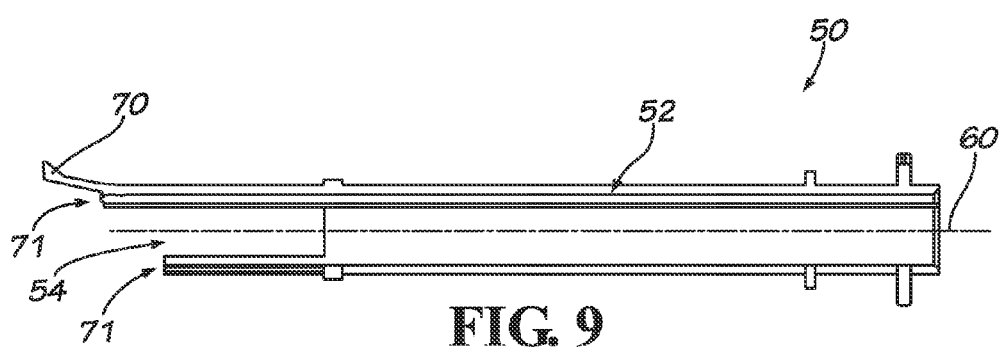
FIG. 9
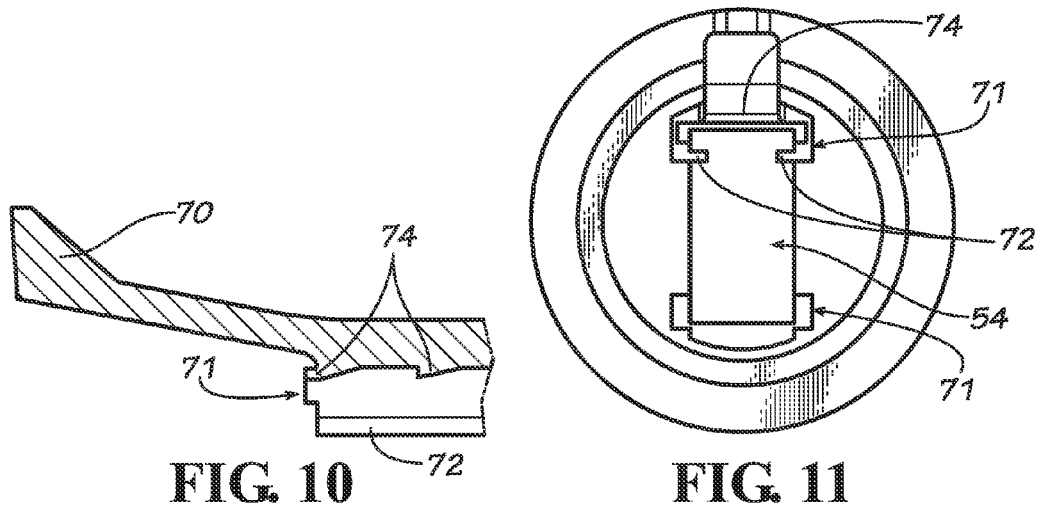
FIG. 10  FIG. 11

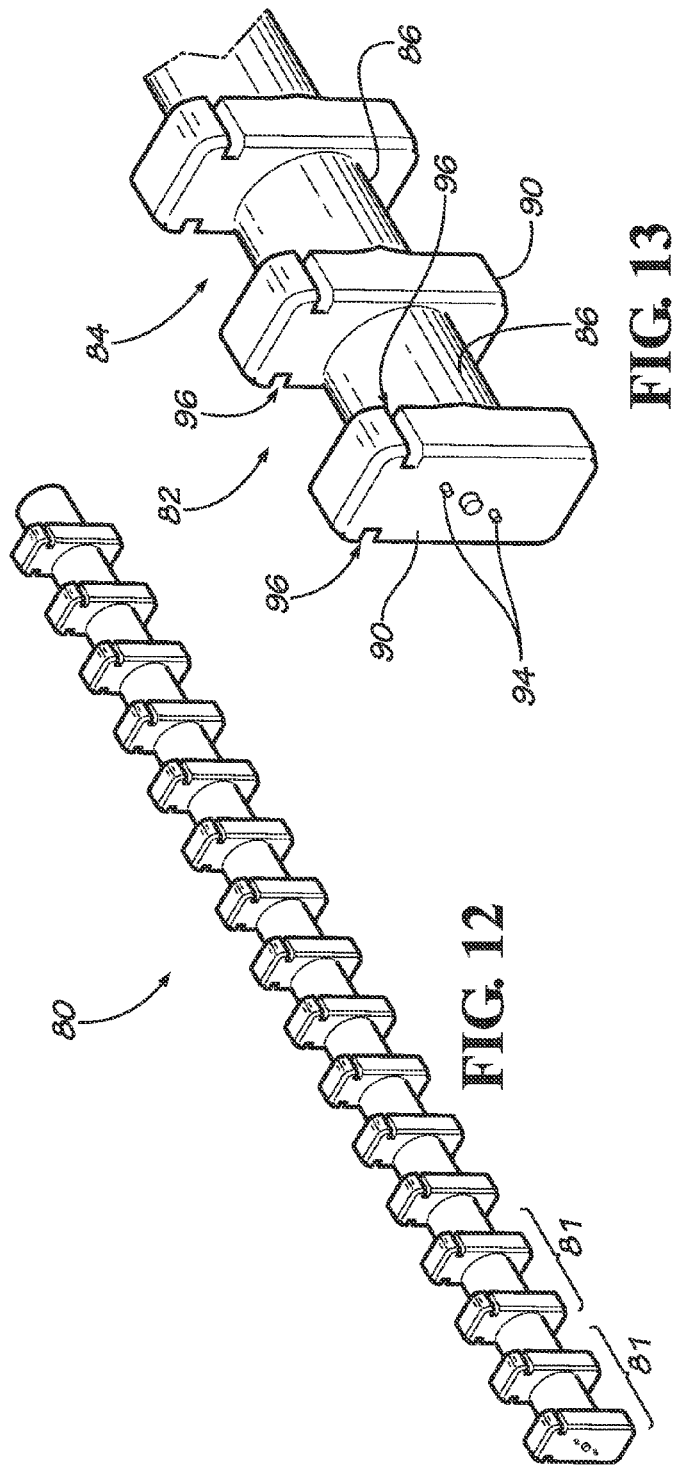
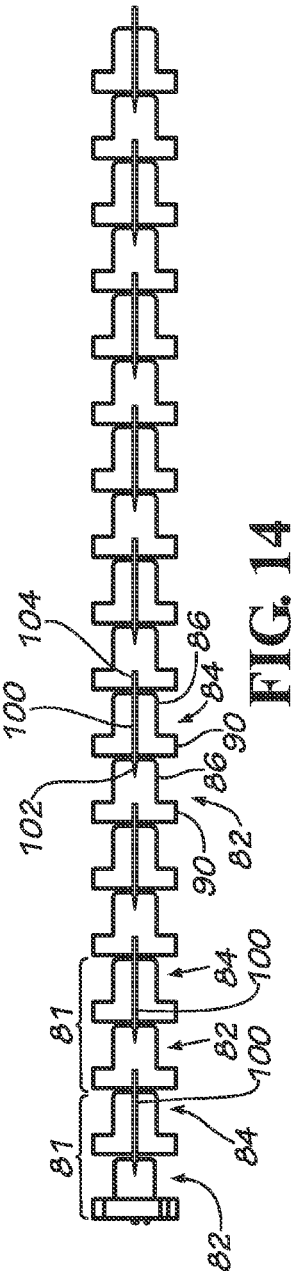
FIG. 12
FIG. 13
FIG. 14

LANCET EJECTION AND ADVANCEMENT MECHANISM FOR MULTI-LANCET CARTRIDGE

CROSS-REFERENCE TO RELATED APPLICATION

This application claims the priority benefit of U.S. Provisional Patent Application Ser. No. 61/843,711 filed Jul. 8, 2013, the entirety of which is hereby incorporated herein by reference for all purposes.

TECHNICAL FIELD

The present invention relates generally to the field of medical devices, and more particularly to lancing devices for blood sampling and testing with mechanisms for advancing and ejecting lancets of a multi-lancet cartridge.

BACKGROUND

Lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism, a charging mechanism for energizing the spring or other drive means of the drive mechanism, and a release mechanism for releasing the drive mechanism upon actuation.

A lancet is typically propelled by the drive mechanism from a retracted position within the housing to an extended position wherein a sharp tip portion of the lancet projects from the housing to prick the subject's skin at a desired lancing site. Optionally, an ejection mechanism may be incorporated into the lancing device for removal of the lancet after use. Many known lancing devices only allow for one lancet to be inserted into the device, which must be removed and replaced each time a sample is desired. It is known that the removal and replacement of the lancet may result in the accidental puncture from the exposed sharp tip portion of the lancet. And, due to the high frequency of use of lancing devices, which is typically multiple times a day per user, the potential for accidental puncture drastically increases. Additionally, because the risk of accidental puncture is known among lancing device users, and accessing a new or unused sterile lancet may be inconvenient to the user, the reuse of non-sterile lancets is quite common and creates a potential for infection.

Accordingly, continuing improvement in the area of ejecting lancets from lancing devices is sought. It is to the provision of improved lancing devices, and advancement and ejection mechanisms, meeting these and other needs that the present invention is primarily directed.

SUMMARY

Generally described, the invention relates to a lancing device including an advance-and-eject mechanism with a positioning member for manipulating a series of interconnected lancing elements. The advance-and-eject mechanism includes an actuator, a control channel, a cam-and-follower mechanism, one or more axial-contact members, and one or more angular-contact members. The lancing elements can include a series of alternating lancets and caps, and the advance-and-eject mechanism operates to sequentially advance and eject the lancing elements during use.

In the depicted embodiment, actuating the actuator relative to the control channel imparts rotational and axial forces on the positioning member, and the cam-and-follower mechanism selectively restricts rotational and/or axial motion of the positioning member to induce first-stage rotation, second-stage translation, third-stage rotation, and fourth-stage translation. The first-stage rotation rotates the axial-contact members into an interference position with the forward-most lancing element, the second-stage translation advances the axial-contact members and the forward-most lancing element, the third-stage rotation rotates the angular-contact members and the forward-most lancing element to sever its rearside connection, and the fourth-stage translation advances the axial-contact members and the forward-most lancing element to a position free of the serial-interconnected lancing elements thereby ejecting it from the lancing device.

In another aspect, the invention relates to advance-and-eject mechanisms, such as those described herein, for inclusion in lancing devices, such as those described herein or others. And in yet another aspect, the invention relates to methods of advancing and ejecting lancing elements, such as lancets and/or caps, such as the herein-described methods of using advance-and-eject mechanisms.

These and other aspects, features, and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description are exemplary and explanatory of typical embodiments of the invention and thus are not unnecessarily restrictive of the invention, as claimed.

BRIEF DESCRIPTION OF THE DRAWINGS

FIG. 4 shows a housing of the lancing device of FIG. 3.

FIG. 5 shows the housing of FIG. 4 with the housing transparent to show hidden internal elements thereof.

FIG. 6 is a top view of the housing of FIG. 5.

FIG. 7 is a perspective-sectional view of a portion of the housing of FIG. 6 taken at line 7-7.

FIG. 8 shows a lancet holder of the lancing device of FIG. 3.

FIG. 9 is a longitudinal cross-sectional side view of the lancet holder of FIG. 8.

FIG. 10 is a side view of a portion of the lancet holder of FIG. 9, showing its lancet-retention elements.

FIG. 11 is a first end view of the lancet holder of FIG. 8.

FIG. 12 shows a multi-lancet chain of the lancing device of FIG. 3.

FIG. 13 shows in detail a portion of the multi-lancet chain of FIG. 12.

FIG. 14 is a longitudinal cross-sectional side view of the multi-lancet chain of FIG. 12.

DETAILED DESCRIPTION OF EXAMPLE EMBODIMENTS

Figure 1:
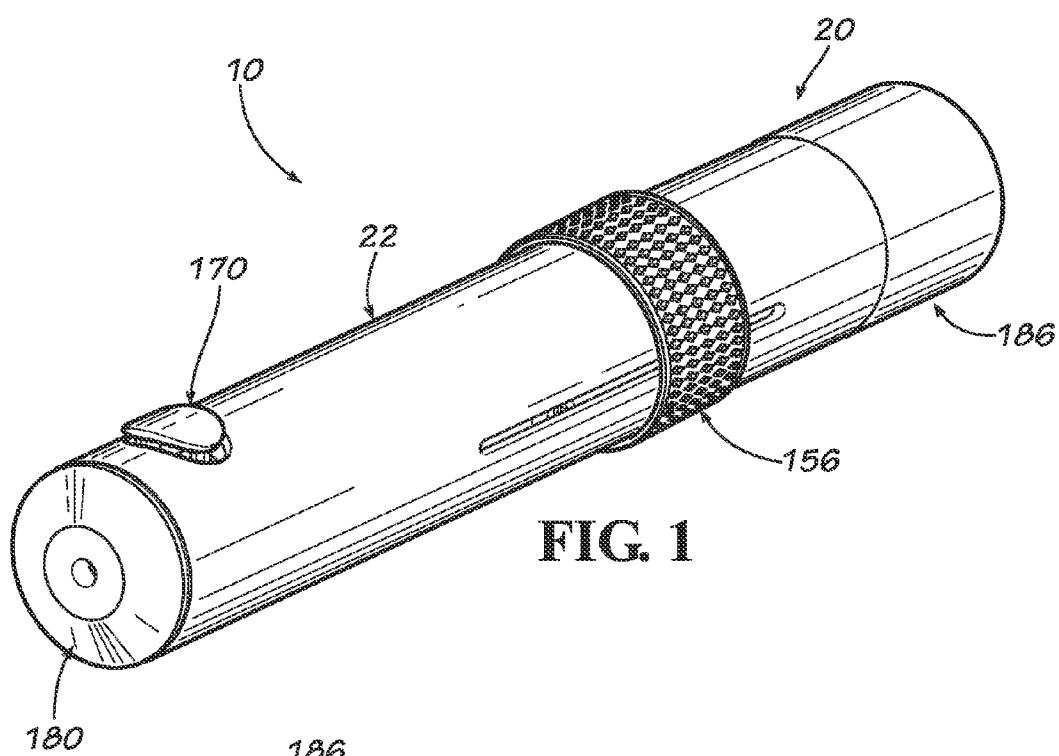
FIG. 1 is a top-right perspective view of a lancing device according to an example embodiment of the present invention.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-25 show a lancing device 10 according to an example embodiment of the present invention. The lancing device 10 is preferably compact, and in the depicted embodiment has a generally cylindrical, narrow-profile, elongate outer geometry, for example having an aspect ratio (length:diameter) of at least 3:1. In other embodiments, the lancing device is disc-shaped, polygonal in cross-section, or otherwise shaped.

Figure 2:
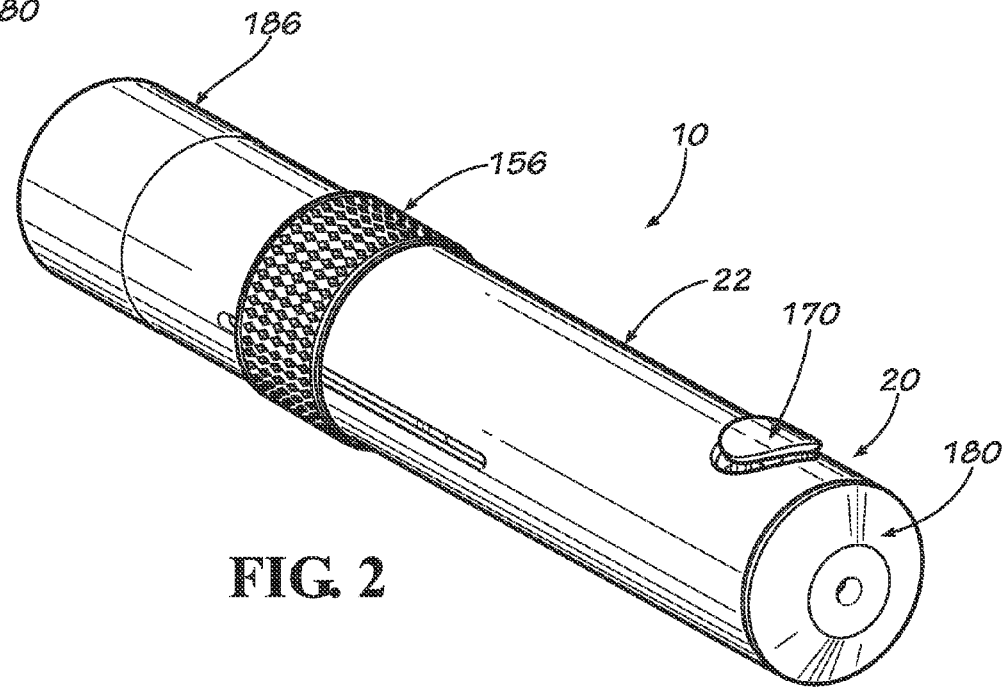
FIG. 2 is a top-left perspective view of the lancing device of FIG. 1.
Figure 3:
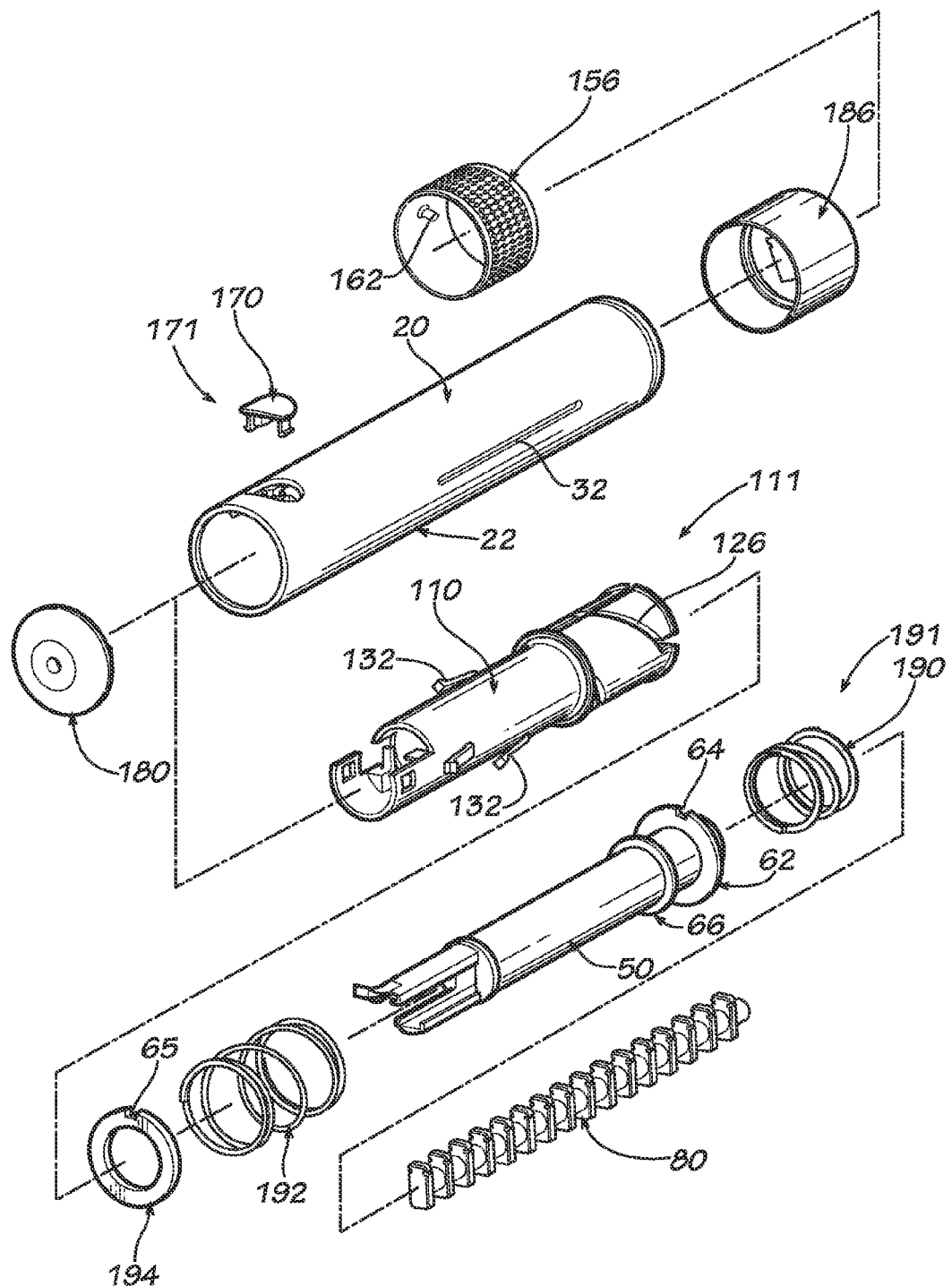
FIG. 3 is an exploded view of the lancing device of FIG. 1 showing the major components thereof.

Referring in particular to FIGS. 1-3, the lancing device 10 includes as major components a housing 20, a lancet holder 50, a drive mechanism 191, a release mechanism 171, and an advancement and ejection mechanism 111 that are operable with a multi-lancet chain 80 of lancets 84. The lancet holder 50 carries the multi-lancet chain 80, the drive mechanism 191 is operable to retract the lancet holder to a charged position and to propel it forward through a lancing stroke, and the release mechanism 171 is operable to release the lancet holder in the charged position to be propelled forward by the drive mechanism. The advancement/ejection mechanism 111 is operable to advance the multi-lancet chain 80 and de-cap its forward-most (use) lancet 84, then it can assist in retracting the lancet holder 50 (and the use lancet) to a charged position. And the housing 20 encloses or supports these major components.

The housing 20 typically includes a main body 22, a front endcap 180, and a rear endcap 186. The rear endcap 186 is typically removable from the main body 22 by a conventional coupling (e.g., a snap-fit coupling or mating screw threads) for loading a new multi-lancet chain 80 for use. In some embodiments, the main body 22 and the rear endcap 186 are provided as one piece, and a different lancet-loading feature is included.

The lancet holder (i.e., lancet carrier) 50 is configured for receiving and holding the multi-lancet chain 80. The lancet holder 50 typically is held in place restrained against axial and rotational movement during advancement and ejection of the lancets 84, but retracted and propelled forward during charging and discharging of the drive mechanism, respectively.

The drive mechanism 191 typically includes a drive spring 190 and a return spring 192 mounted for example on the lancet holder 50. The drive and return springs 190 and 192 drive the lancet holder 50 (and the front lancet 84 in the use position) through a lancing stroke from a charged position within the housing 20 to a lancing position in which a sharp tip portion of the use lancet projects through the front endcap 180 to prick the subject at a lancing site. In other embodiments, the drive-spring functionality and the return-spring functionality are provided by a single spring. The release mechanism 171 includes a release button 170 that is operable to disengage the lancet holder 50 from the housing 20 thereby releasing the lancet holder from retention in its charged position.

The advancement/ejection mechanism 111 includes an advancement and ejection positioning member (a positioner) 110 and an actuator 156. The actuator 156 is operable to drive the positioner 110 to sequentially advance, de-cap, and eject the use-positioned lancet 84 of the multi-lancet chain 80, as will be described in greater detail below. The multi-lancet chain 80 is positioned within the lancet holder 50, which is typically positioned generally within (e.g., coaxially) the positioner 110, which is typically positioned generally within (e.g., coaxially) the housing 20.

FIGS. 4-7 show the housing 20 in greater detail. The housing body 22 is typically generally cylindrical-shaped with an open front end 26 and an open rear end 27, though other shapes and configurations can be used. (As used herein, front and forward ends or portions means that which is closer to the lancing site, and rear or rearward ends or portions means the opposite.) The housing body 22 includes a bore 24 extending axially therethrough along a longitudinal axis 30, and the lancet holder 50 and the positioner 110 are received in the housing bore. A release opening 31 is formed through the housing body 22, for example radially through the body near its first end 26, for receiving therethrough the release button 170 that can be actuated to selectively disengage a portion of the lancet holder 50 from a portion of the housing 20, thereby freeing the lancet holder to move from the charged position to the lancing position.

Some features of the advance/eject mechanism 111 are typically provided as integral components of the housing 20. In the depicted embodiment, one or more (e.g., two opposing ones, as depicted) control slots 32 penetrate through the housing body 22 and extend along its axis 30. The housing control slots 32 receive a respective number (e.g., two opposing ones, as depicted) of control pins 162 of the actuator 156 to provide control of the actuator when it is driven through a forward operating and rearward return motion, and at the same time they enable the actuator control pins to extent through the housing 20 to engage a respective number (e.g., two opposing ones, as depicted) of control channels 126 in the positioning member 110 to drive the positioning member through sequential rotational and translational motion stages to advance and eject the lancets 84 of the multi-lancet chain 80, as described below. The housing control slots 32 are typically generally linear to provide generally translational (axial) control of the actuator 156 while the positioner control channels 126 (see FIG. 16) are typically generally helical to impart the rotational and translational forces on the positioner 110, as depicted. In other embodiments, the housing control slots are generally helical or circumferential and the positioner control channels are generally linear for providing the same positioner-motion functionality described herein.

In addition, one or more (e.g., two opposing ones, as depicted) guide or motion-restricting cams 40 are formed along the inner surface of the housing body 22, typically extending from adjacent the front end 29 of its housing control slots 32 to adjacent its housing front end 26. The guide cams 40 are engaged and tracked by respective (e.g., two opposing ones, as depicted) cam followers 132 of the positioner 110 to dictate precise translational and rotational movement of the positioner to advance and eject the lancets 84 of the multi-lancet chain 80, as described below. The guide cams 40 can be in the form of protruding ribs (as depicted), recessed grooves, stepped sidewall structures, or other guide tracks.

The guide or motion-restricting cams 40 of the housing 20 each include a first segment 42 that causes rotation of the positioner 110 in a first angular direction in a first motional stage, a second segment 44 that causes translation of the positioner in a forward direction in a second motional stage, and a third segment 46 that causes further rotation of the positioner in the first angular direction in a third motional stage. As such, the cam first segment 42 restricts (i.e., eliminates or reduces to a negligible/nominal amount) translation of the positioner 110 and thereby induces it to rotate. In the depicted embodiment, for example, the cam first segment 42 is generally circumferential (a slight helical curve/angle is provided to avoid binding and induce rotation of the positioner 110 in the first angular direction while providing a negligible/nominal amount of positioner translation) and provided by a single rib against which the positioner cam followers 132 are driven and guided. The cam second segment 44 restricts rotation of the positioner 110 and thereby induces it to translate. In the depicted embodiment, for example, the cam second segment 44 is generally axial and provided by parallel ribs between which the positioner cam followers 132 are driven and guided. And similarly to the cam first segment 42, the cam third segment 46 restricts translation of the positioner 110 and thereby induces it to rotate. In the depicted embodiment, for example, the cam third segment 46 is generally circumferential (a slight helical curve/angle is provided) and provided by a single rib against which the positioner cam followers 132 are driven and guided.

A fourth motional stage of further translation of the positioner 110 in the forward direction can be caused by the actuator control pins 162 pushing forward against the front ends 29 of the housing control slots 32, as depicted, or alternatively by fourth segments of the guide cams that are arranged similarly to the cam second segments 44. In some embodiments, the fourth-stage translational motion is not provided, for example as described below.

FIGS. 8-11 show the lancet holder 50 in greater detail. The lancet holder 50 comprises a generally elongate body 52 that extends from an open front end 56 to an open rear end 57 and defines an internal bore 54 along a longitudinal axis 60. Alternatively, the lancet holder can have a polygonal, rectangular, or other cross-sectional shape, a peripheral wall and/or bore not extending along its entire length, and/or another form such as a frame, channel, plate, or another conventional lancet holder or carrier.

A drive flange 62 extends radially outward from the elongate body 52 and is engaged by the drive spring 190 to drive the lancet holder 50 through the forward portion of the lancing stroke. The drive flange 62 can be in the form of a circumferential flange, as depicted, or by another protrusion extending transversely outward (e.g., radially) from the elongate body. In typical embodiments, the drive flange 62 is positioned proximal the second end 57 of the elongate body 52, with the drive spring 190 positioned between and biasing against the drive flange and the rear endcap 186 of the housing 20.

In addition, a return flange 194 extends transversely outward (e.g., radially) from the elongate body 52 and is engaged by the return spring 192 to drive the lancet holder 50 through the return portion of the lancing stroke (see FIG. 3). The return flange 194 can be in the form of a circumferential flange, such as the depicted removable washer, or by another protrusion extending transversely outward from the elongate body. In typical embodiments, the return flange 194 is positioned forward of the drive flange 62, with the return spring 192 positioned between and biasing against the return and drive flanges. Thus, the drive and return springs 190 and 192 retain the lancet holder 50 in a neutral position biased against forward (or rearward) translational motion during the advance/eject operation of the positioning member 110.

A mechanical stop 66 is provided for limiting the forward travel of the lancet holder 50. For example, the mechanical stop 66 can be in the form of the depicted stop flange, with the return flange 194 translationally slideable along the lancet-holder body 52 to charge the return spring 192 during the forward portion of the lancing stroke to provide a soft stop.

Furthermore, the lancet holder 50 and the housing 20 include cooperating guidance elements that translationally guide the lancet holder through its lancing stroke. For example, the guidance elements can be provided by notches 64 and/or 65 in the drive and/or return flanges 62 and 194 that slidingly receive an axial rib 67 along the inner wall of the housing 20 (extending into its bore 24) to allow only axial movement of the lancet holder 50 relative to the housing (see FIG. 5). As such, the cooperating guidance notches 64 and 65 and rib 67 prevent rotational movement of the lancet holder 50 relative to the housing 20 during the lancing stroke and during the advancement and ejection of the lancets 84. Alternatively, the notches can be formed on another part of the lancet holder, the notch-and-rib arrangement can be reversed (i.e., rib/protrusion on lancet holder and notch/groove on housing), or other conventional lancet axial-guidance structures can be provided.

The release mechanism 171 includes cooperating catch elements of the lancet holder 50 and the housing 20 that are releasably engageable for holding the lancet holder in the charged position and then releasing it to travel along the lancing path under the discharging influence of the drive spring 190. For example, the releasable catch elements can be provided by a cantilever catch finger 70 proximal the first end 56 of lancet holder 50 that catches on a catch lip of the release opening 31 in the housing 20 to retain the lancet holder in the charged position. The lancet-holder cantilever finger 70 is spring-biased into a catching engagement with the housing release opening 31, with the spring force provided by deflection of the cantilever finger. The lancet-holder cantilever finger 70 can be displaced and thus disengaged from the lip of the housing release opening 31 for example by being contacted by a releasing element 176 of the release button 170.

In this embodiment, the cantilever finger 70 of the lancet holder 50 has a front end that can impact the front endcap 180 to function as a hard mechanical stop to the forward portion of the lancing stroke of the lancet. This can be provided in addition to or as an alternative to the soft mechanical stop 66 described below. Alternatively, the lancet holder catch element can be provided by a cantilever finger that does not extend forward of the lancet-retention detents, the lancet holder catch element can be provided by another spring-biased structure such as a pin biased by a coil spring, the housing catch element can be provided by a portion of the release button, or other conventional lancet catch-and-release structures can be provided.

The lancets 84 of the multi-lancet chain 80 are received in the bore 54 of the lancet holder 50 and advanced axially through it by operation of the advance/eject mechanism 111. To retain the multi-lancet chain 80 in the proper angular position, the lancet holder 50 can include angular-positioning elements. For example, the angular-positioning elements can be in the form of two opposing jaw or guide-wall members 71 (e.g., the depicted top and bottom U-shaped/channel members), or alternatively by peripheral walls (surrounding the lancets 84) or other structures that keep the lancets in the proper angular position as they are advanced forward through the lancet-holder 50. To provide such proper angular positioning, at least a portion of the periphery of the lancet-holder bore 54 defined by and between the guide-wall jaw members 71 has a shape and size generally conforming to that of the lancets 84. For example, the bore 54 can be generally rectangular, as shown in FIG. 11. In addition, one or more (e.g., the two depicted ones) of the guide-wall members 71 can include guidance elements such as inwardly-extending guide fingers 72 for cooperating engagement with a portion of the multi-lancet chain 80, as described below.

In addition, the lancet holder 50 typically includes one or more (e.g., the two depicted) retention elements that apply forces on the lancets 84 of the multi-lancet chain 80 to axially bias them into and retain them in a retained position where they can be engaged by the advance/eject mechanism 111 for advancement and ejection. For example, the retention elements can be in the form of front and rear detents 74 extending into the bore 54, such as the depicted unidirectional ramped detents extending from the top guide-wall member 71. With such unidirectional ramped detents 74, the lancets 84 can easily be advanced forward (across the ramped surface to slightly deflect the top guide-wall member 71) during normal advancement for use, but they cannot be easily retracted rearward (due to interference with the non-ramped/transverse surface) if the lancing device 10 is accidentally dropped or jostled or due to an opposing force on the lancets from pricking the skin (see also FIG. 15).

FIGS. 12-14 show the multi-lancet chain 80 in greater detail. The multi-lancet chain 80 includes a series of lancing elements 81, each including a lancet 84 and a sterility cap 82. Thus, the lancets 84 and sterility caps 82 are arranged in an alternating fashion, with each one of the lancet caps (except the first one) connected to the front and back of trailing and preceding ones of the lancets, respectively, and with each one of the lancets connected to the front and back of trailing and preceding ones of the caps, respectively, to form the multi-lancet chain 80. In this embodiment, the alternating lancing elements (i.e., the lancets and the caps) are sequentially advanced within and ejected from the lancing device. In other embodiments, the lancing elements include only the lancets, without the caps. In such embodiments, the terms lancing element and lancet are interchangeable.

The caps 82 and the lancets 84 of the depicted embodiment each have a body portion 86 and a transverse flange portion 90, with the flanges having a common size and shape for being engaged by the advance/eject mechanism 111. (As such, reference herein to advancing and ejecting the lancets 84 also means advancing and ejecting the caps 82.) For example, the bodies 86 can be generally cylindrical (e.g., coaxial with the lancing stroke) and the flanges 90 can extend generally transverse to the respective bodies (e.g., to the cylindrical-body axis) and be generally rectangular. To provide for guidance of the multi-lancet chain 80 through the lancet holder 50, the lancet and cap flanges 90 can include guidance elements that cooperate with the lancet-holder guidance elements, for example one or more (e.g., the two depicted) grooves 96 for slidingly receiving and guiding the guide fingers 72 of the lancet holder.

The lancets 84 each include a lancing needle 100 with a front sharp tip section 102 extending forward from its lancet flange 84 (and thus received in the preceding cap body 86) and with a rear connecting section 104 opposite its tip and extending rearward from its lancet body (and thus received in the trailing cap flange). In this way, with the needle tip sections 102 extending into the preceding cap body 86 and the needle rear sections 104 extending into the trailing cap flange 90, the lancets 84 and caps 82 in the chain 80 are all interconnected in a structurally rigid fashion such that, when holding the multi-lancet chain 80 (e.g., by one end portion)

and loading it into the lancing device 10, it remains generally rigid such that it does not come apart and the breakaway connections 94 (discussed immediately below) are not stressed and/or caused to prematurely fail. Typically, the lancet body 86 and flange 90 are molded with the needle 100 extending through and fixed to them, with the needle defining the lancing stroke axis and thus with the tip 102 and rear 104 providing negligible (little or no) torsion-resisting and/or axial-pull-resisting forces on the trailing and leading caps 82, respectively, that they are removably received in.

In addition, the lancets 84 and the caps 82 can be interconnected to each other by one or more (e.g., the two depicted) breakaway connections 94 to retain them in position relative to each other (i.e., to provide torsion-resisting and/or axial-pull-resisting forces). The breakaway connections 94 are typically in the form of attachment webs, for example relatively thin bodies or protrusions that extend between adjacent bodies 86 and flanges 90 and that can be broken (e.g., caused to structurally fail) by applying a torsional and/or tensional force to one of the lancets 84 or caps 82 while holding the adjacent connected lancet or cap. Typically, at least two breakaway connections 94 are provided for each connection, arranged in a transversely spaced-apart relationship and not axially aligned with the needle 100, and positioned on a transverse surface of one of the bodies 86, thereby resisting torsional and axial forces on the lancets 84 and caps 82.

In other embodiments, the lancets do not include the rear connecting sections of their needles, with the lancets and caps interconnected by the breakaway connections 94 (and to some extent the lancet tips 102). In yet other embodiments, the lancets do not include the breakaway connections, and the lancets and caps are interconnected only by the tip sections 102 and rear sections 104 of their needles 100. In some embodiments, the multi-lancet chain includes only the lancets 84, with the body 86 of each lancet also serving as a cap by receiving and covering the tip 102 of the needle 100 of the trailing lancet. And in some embodiments, the multi-lancet chain 80 includes a cartridge such as casing or frame that houses or otherwise rigidly supports the lancets 84 and caps 82.

As just one example, in an alternative embodiment the lancets do not include the rear sections of their needles, and the lancets and caps are interconnected by the breakaway connections and/or by a support frame of the multi-lancet chain. Because a used lancet does not need to be advanced to clear its rear section from a trailing cap during ejection, the advance/eject mechanism can be designed for not providing the fourth-stage translation motion, and instead the third-stage rotation separates and also ejects the used lancet. In some such embodiments, the caps can include curved channels that receive the needle tips of the trailing lancets for use with the same design without the fourth-stage translation motion.

Figure 15:
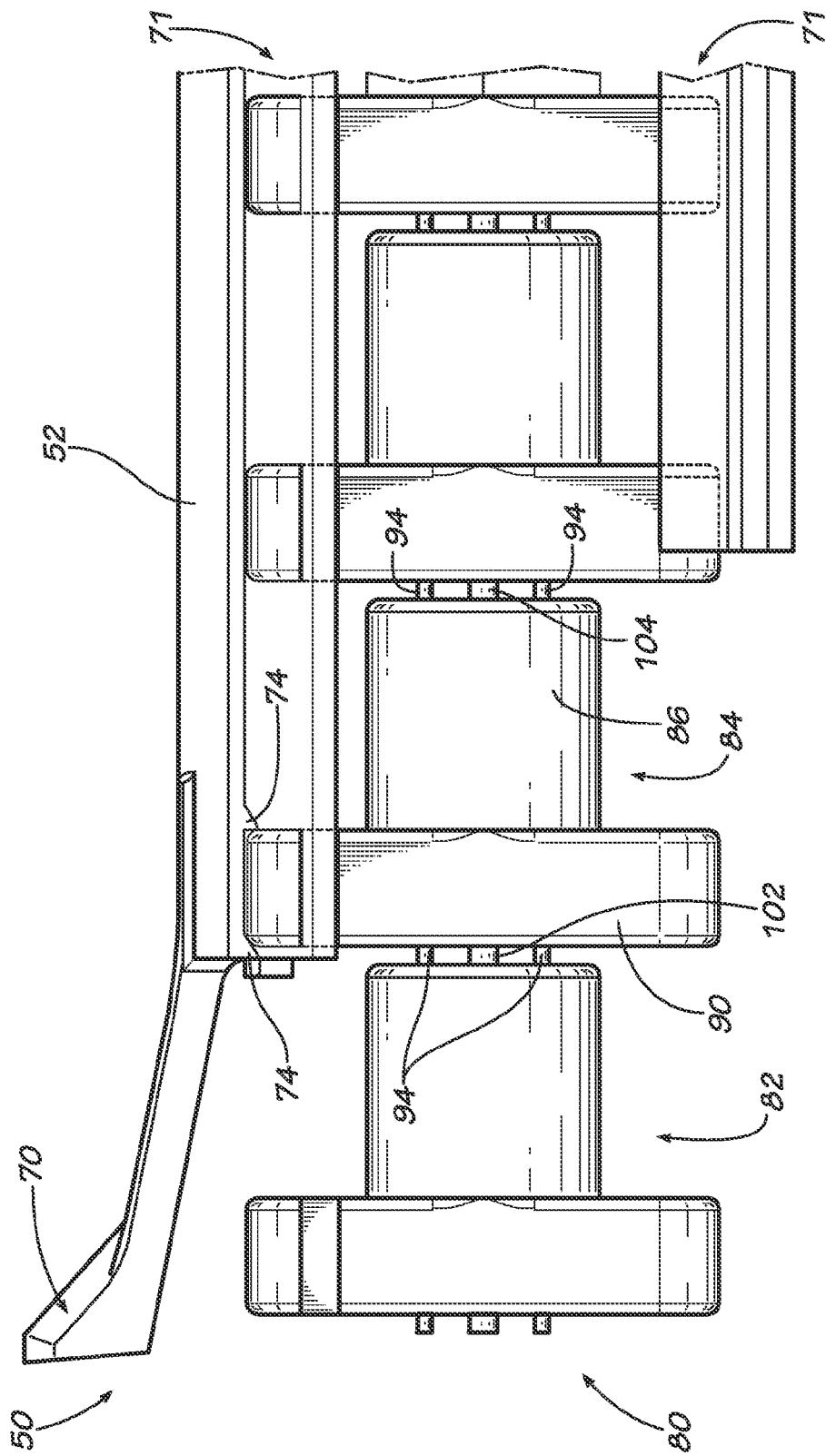
FIG. 15 is a side view of the lancet holder of FIG. 8 and the multi-lancet chain of FIG. 12, showing a lancet flange of the multi-lancet chain removably engaged with the lancet-retention elements of the lancet holder in a ready position.
Figure 16:
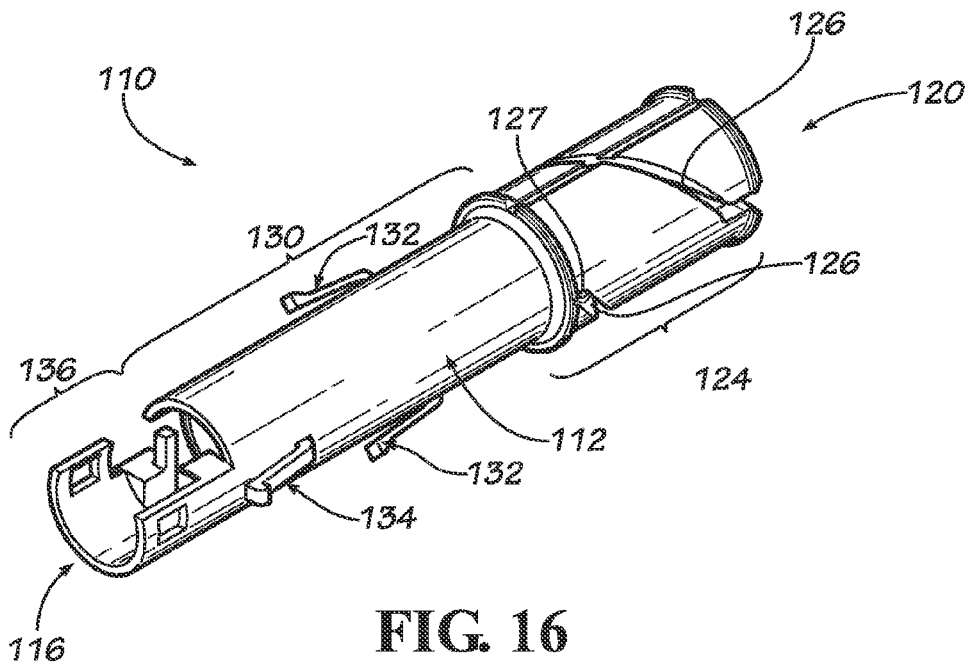
FIG. 16 shows a positioning member of the lancing device of FIG. 3.
Figure 17:
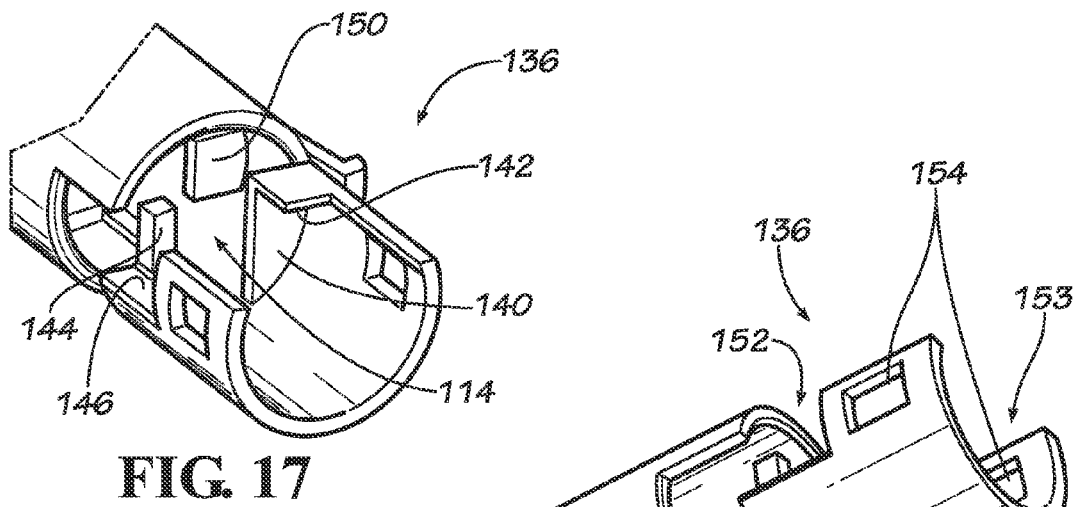
FIG. 17 is a top perspective view of a portion of the positioning member of FIG. 16.
Figure 18:
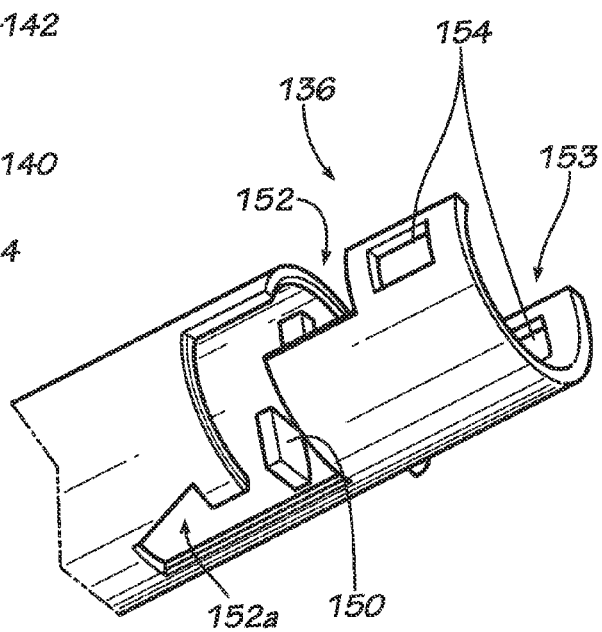
FIG. 18 is a bottom perspective view of the positioning member portion of FIG. 17.
Figure 20:
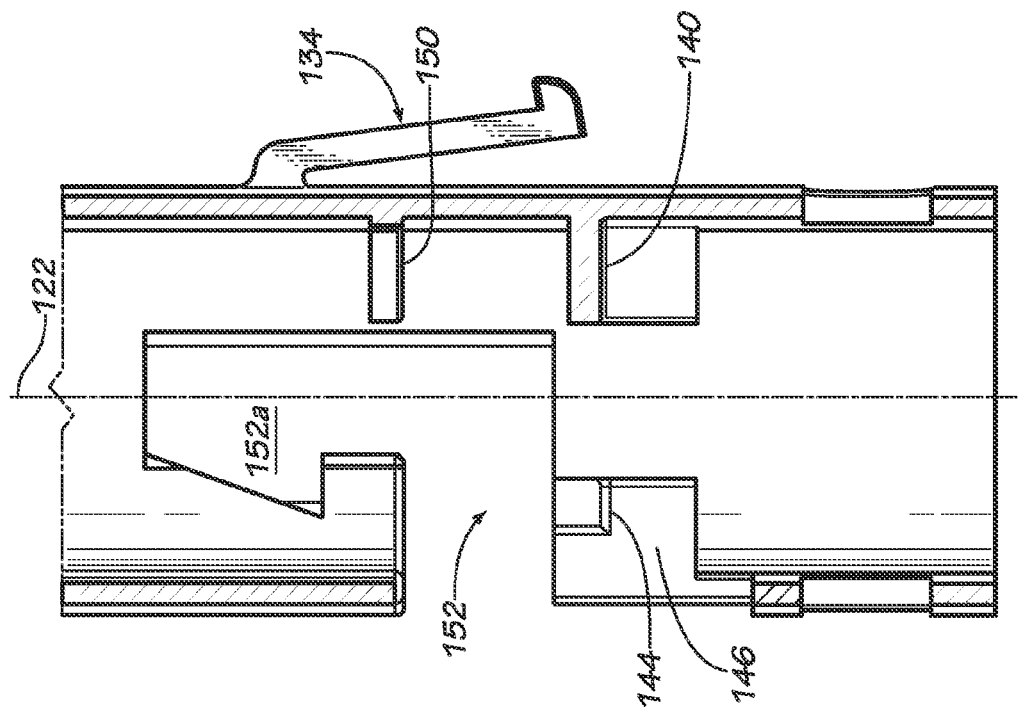
FIG. 20 is a longitudinal cross-sectional view of the positioning member of FIG. 19 taken at line 20-20.
Figure 19:
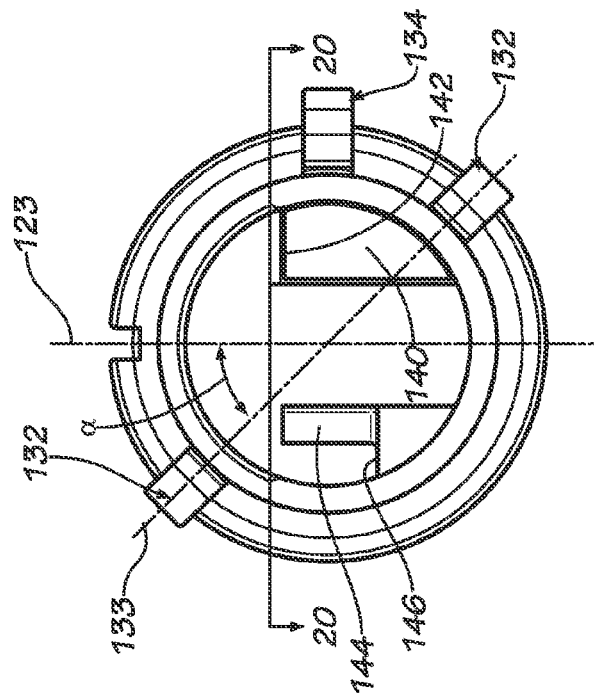
FIG. 19 is a first end view of the positioning member of FIG. 16.

FIG. 15 shows the multi-lancet chain 80 positioned within the bore 54 of the lancet holder body 52 for advancement by the advance/eject mechanism 111. A first one of the lancing elements 81 (a cap 82) has been advanced to a use position, forward of a retained position, by operation of the advance/eject mechanism 111. And a second one of the lancing elements 81 (a lancet 84) is now in a retained position, with its lancet flange 90 engaged by the ramped detents 74 (or other lancet-retention elements) of the lancet holder 50. The first/use cap 82 is now ready to be advanced, separated from the trailing lancet 84, and ejected from the housing 20 by operation of the advance/eject mechanism.

In other embodiments, the use position is defined by the lancing element being retained by the lancet-retention elements (e.g., ramped detents) 74. In such embodiments, the releasable catch element (e.g., cantilever finger) 70 of the lancet holder 50 is configured so that it does not extend forward beyond the lancet-retention detents 74.

FIGS. 16-20 show the positioning member 110 in greater detail. The positioning member 110 is configured to movably mount within the bore 24 of the housing 20 to either translate or rotate depending upon the particular stage of engagement with the motion-dictating guidance cams 34 of the housing. The positioning member 110 includes an elongate cylindrical body 112 that extends from an open front end 116 to an open rear end 120 and that defines a bore 114 extending axially through the body 112 along a longitudinal axis 122, with the lancet holder 50 being received and axially movable therein. Alternatively, the positioning member can have a polygonal, rectangular, or other cross-sectional shape, a peripheral wall and/or bore not extending along its entire length, and/or another form such as a frame, channel, plate, or other structure for providing the functionality described herein.

In the depicted embodiment, the positioning member 110 includes a drive portion 124, a guide or motion-restricting portion 130, and a lancet-engaging portion 136. These portions are labeled in this way for ease of reference only, and the structural features described herein in each of them can alternatively be located on another portion of the positioning member 110.

The drive portion 124 of the positioning member 110 can include for example the positioner helical control channels 126 that receive the actuator control pins 162 (which extend through the housing control slots 32) to drive the positioning member 110 through sequential rotational and translational motion stages to advance and eject the lancing elements 81 (alternating lancets 84 and caps 82) of the multi-lancet chain 80, as described below. The helical control channels 126 are typically formed as surface grooves, though they can be provided as slots that penetrate through to the internal bore 54 of the positioner member 110. The pins 162 of the actuator 156 extend through the control slots 32 of the housing 20 and into the helical guide channels 126 of the positioner 110, and when the actuator is moved axially forward relative to the housing 20, the positioner is forced to rotate or translate therein, as discussed herein. The pitch of the helical guide channels 126 can be selected to set the translation-to-rotation ratio of the actuator 156 movably mounted thereto.

The guide or motion-restricting portion 130 of the positioning member 110 can include for example the guide or motion-restricting cam followers 132. The cam followers 132 cooperatively engage the guide or motion-restricting cams 40 of the housing 20 to convert the operating motion of the actuator 156 into the desired rotational and/or translational motion of the positioner 110 (as dictated by the segment of the cams engaged) to advance and eject the lancets 84 of the multi-lancet chain 80, as described below. As such, the cam followers 132 are typically provided by a respective number (e.g., the depicted two) of protrusions (for contacting and following along the cam rib sections, as depicted), recessed grooves, stepped sidewall structures, or other guide-track followers. In the depicted embodiment, for example, the cam followers 132 are each in the form of a cantilever including an arm extending from the positioner body 112 along its longitudinal axis and a head extending therefrom so that the head follows one of the positioner cams 40 and the arm can deflect slightly outward (e.g., radially) to maintain good contact of the head against the respective cam. Also, the cam followers 132 can be positioned oppositely each other on the positioner body 112 defining a tilted transverse diameter line 133 that is at an angle α relative to a vertical transverse diameter line 123, with the vertical transverse diameter line defining a first angular position of the positioner 110 and the lancets 84, and with both lines being transverse to the longitudinal axis 122 of the positioner body (see FIGS. 19-20).

In addition, a guide or motion-restricting retraction element 134 can be included for example on the guide or motion-restricting portion 130 of the positioner 110. The retraction element 134 is provided for movably engaging an axial-motion-restricting element of the housing 20 during a first stage of a rearward return motion of the actuator 156, after its forward operating motion to accomplish the rotation and translation of the positioner 110 to effect the advancement and ejection of one of the lancets 84 or caps 82. The retraction element 134 movably engages the axial-motion-restricting element of the housing 20 to permit reverse rotation of the positioner 110, but not reverse translation, in response to the first return stage of the actuator 156. This causes the positioner 110 to return to its first angular position in which it is clear of axial movement of the lancets 84 along the lancing stroke. An axial-motion-permitting element of the housing 20 (e.g., the ramp 48 depicted) is then engaged by the retraction element 134 to permit reverse axial movement of the positioner 110 during a second stage of a rearward return motion of the actuator 156.

In the depicted embodiment, for example, the retraction element 134 is in the form of a cantilever and the axial-motion-restricting element is provided by the front end (i.e., the front edge or lip) 26 of the housing 20, with the cantilever including an arm extending from the positioner body 112 along its longitudinal axis and a head extending therefrom so that when extended axially forward the head catches on the housing front end (to prevent axial retraction) and the arm can deflect slightly outward (e.g., radially) to maintain good contact of the head on housing front end during the first return stage. And the axial-motion-permitting element of the housing 20 is in the form of a ramp 48 at the housing front end 26 that permits axial retraction of the cantilever head 134 during the second return stage of the actuator 156 (see FIGS. 32A-32C).

The lancet-engaging portion 136 of the positioning member 110 can include for example features for advancing the multi-lancet chain 80 and ejecting the lancing elements 81 (the caps 82 and lancets 84). In particular, one or more axial contact members and one or more angular contact members extend from the positioner body 112 into the positoner bore 114, the axial contact members configured for axially advancing the lancets 84 and the angular contact members configured for rotating the lancets. The axial and angular contact members are typically provided by flanges, plates, bars, pins, or other members extending inward from the positioner body 112 into the positoner bore 114 to provide the functionality described herein.

In the depicted embodiment, for example, the positioner 110 includes three axial contact members in the form of two forward walls 140 and 144 and one rear wall 150. The two forward axial-contact walls 140 and 144 are positioned on opposite sides (e.g., left and right) of the multi-lancet chain 80, and with these walls arranged in a transverse plane, transversely aligned, and facing axially forward. The two forward axial-contact walls 140 and 144 are positioned axially rearward of the use-positioned (i.e., first or forward-most) lancet or cap flange 90, and the rear axial-contact wall 150 is positioned axially rearward of the retained (i.e., second, trailing, or second-most-forward) lancet or cap flange. And this embodiment includes two angular contact members in the form of two walls 142 and 146, with these two walls positioned on opposite sides (e.g., top and bottom) of the multi-lancet chain 80, and with each of these walls facing transversely (relative to axially forward). The angular contact wall 142 and the forward axial contact wall 140 can be adjacent and integrally formed together as a single generally L-shaped structure, and the angular contact wall 146 and the forward axial contact wall 144 can be adjacent and integrally formed together as a single generally L-shaped structure, as depicted.

In other embodiments in which the use position is defined by the lancing element being retained by the ramped detents, the rear axial-contact member is not included, and the axial-contact and angular-contact members engage and manipulate the use/retained lancing element. Additional details of such an alternative embodiment are described above with reference to FIG. 15.

Figure 27A:
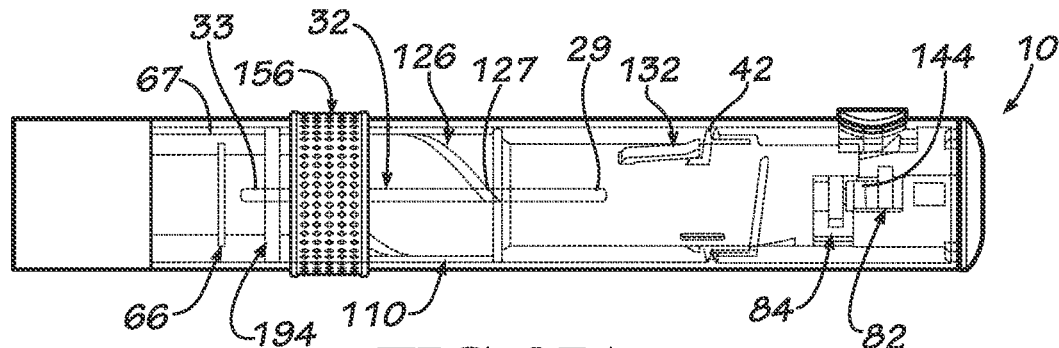
FIGS. 27A-27C are a side, perspective partial, and front views, respectively, of the lancing device of FIG. 1, showing an advancement and ejection mechanism in a ready or first position.
Figure 27B:
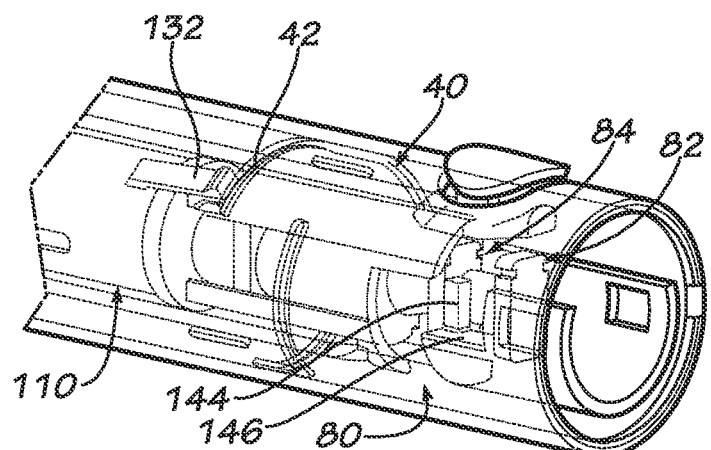
Figure 27C:
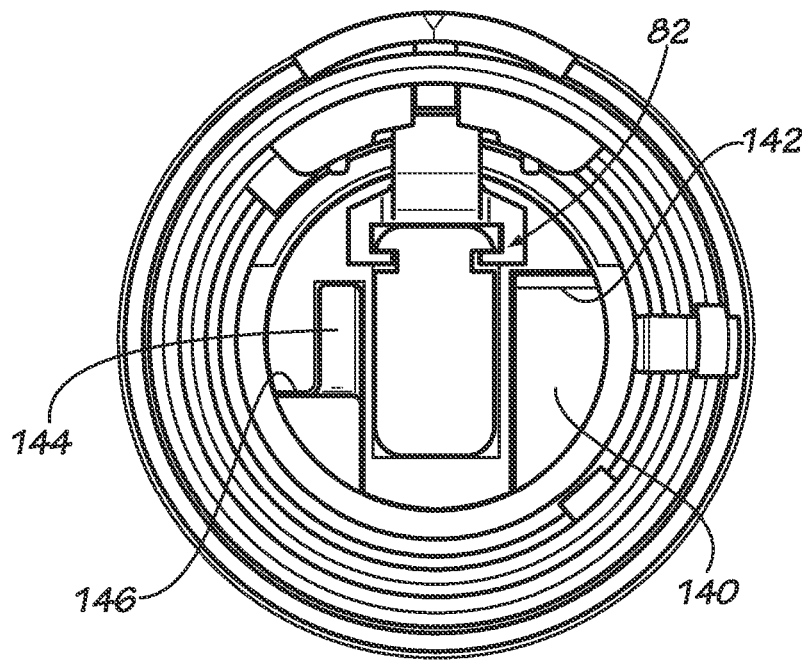
Figure 28A:
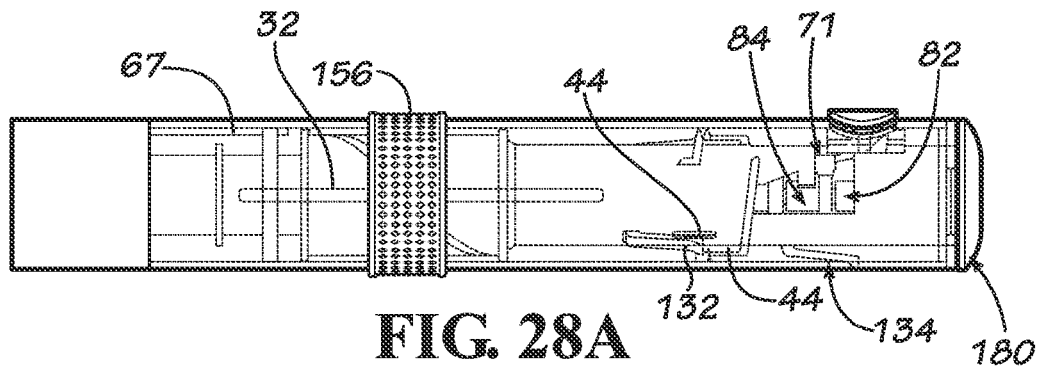
FIGS. 28A-28C show the lancing device of FIGS. 27A-27C, respectively, with the advance/eject mechanism in a second position with axial-contact elements rotated into an interference position.
Figure 28B:
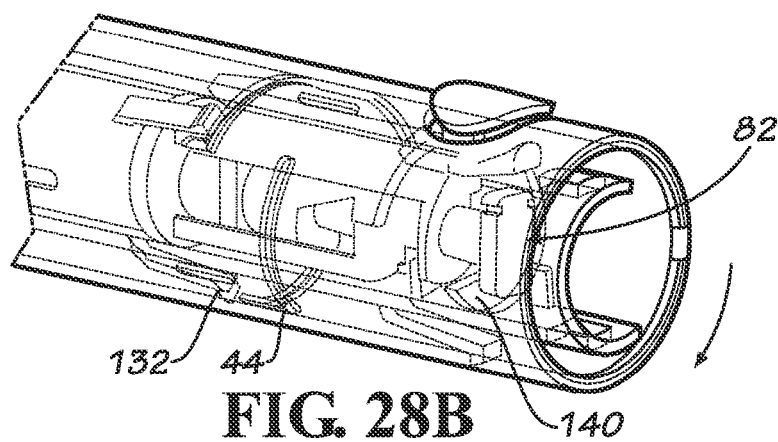
Figure 28C:
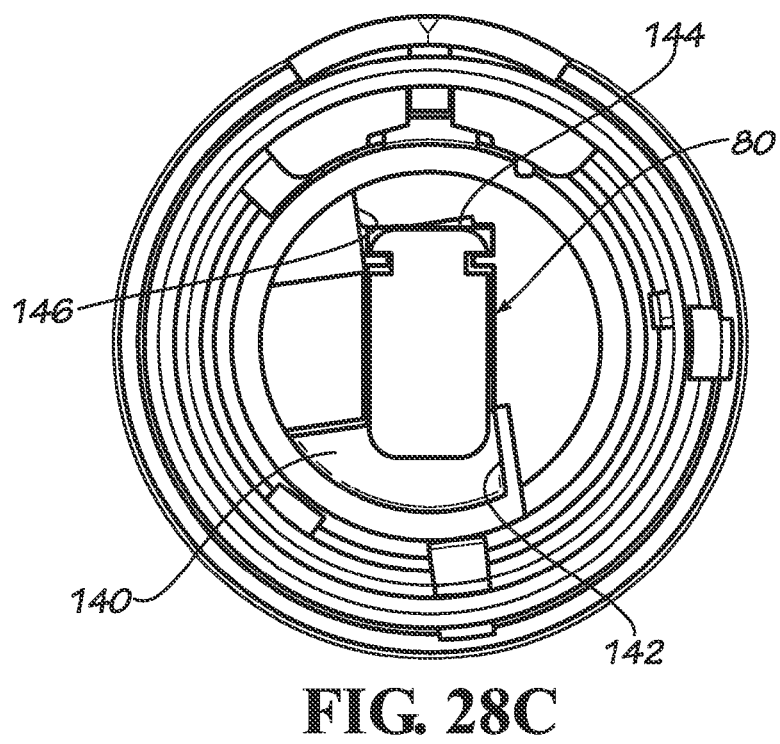
Figure 29A:
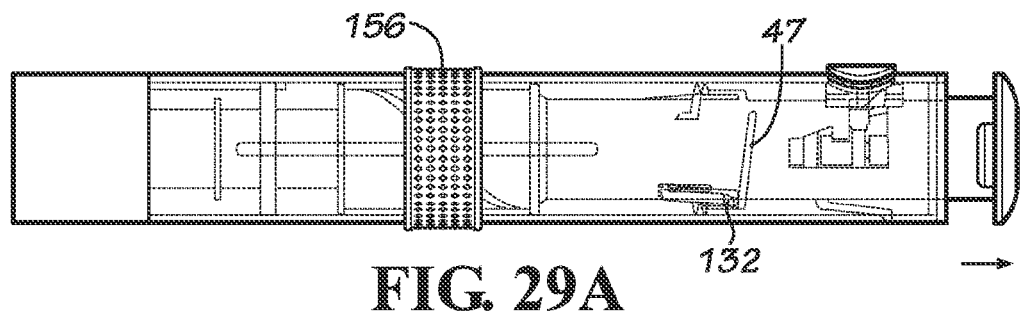
FIGS. 29A-29C show the lancing device of FIGS. 27A-27C, respectively, with the advance/eject mechanism in a third position with the axial-contact elements advanced to advance the forward-most lancing element.
Figure 29B:
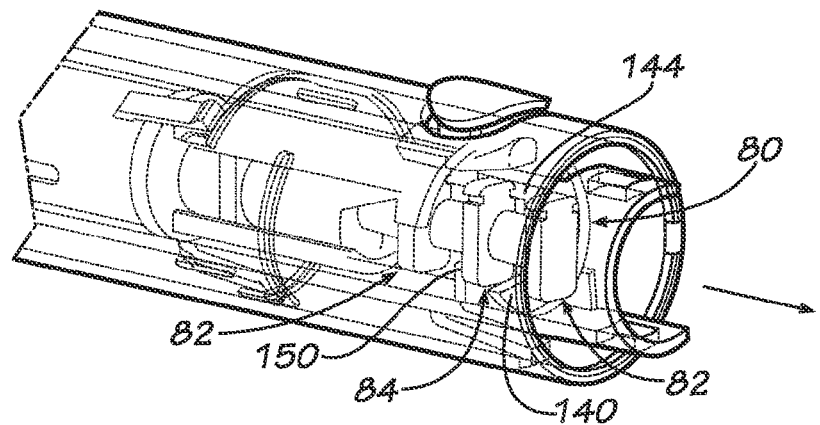
Figure 29C:
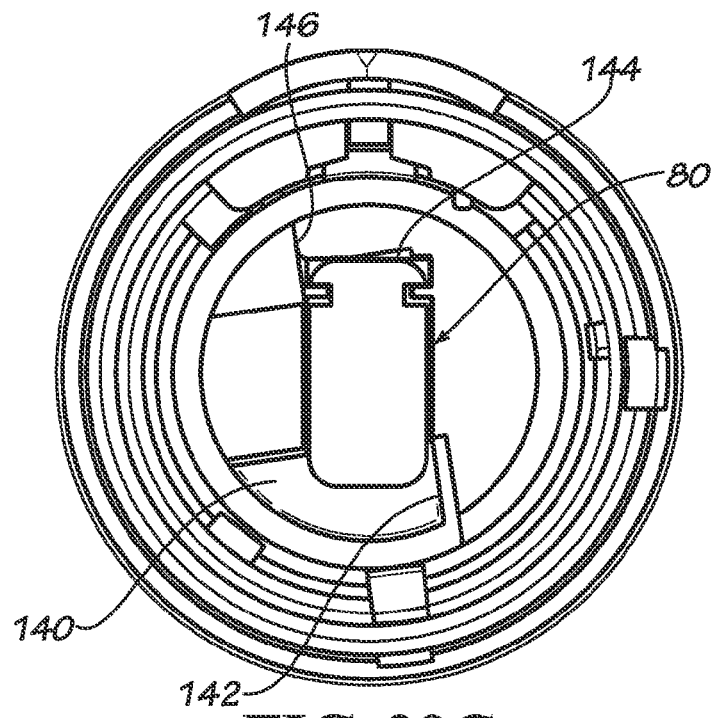
Figure 30A:
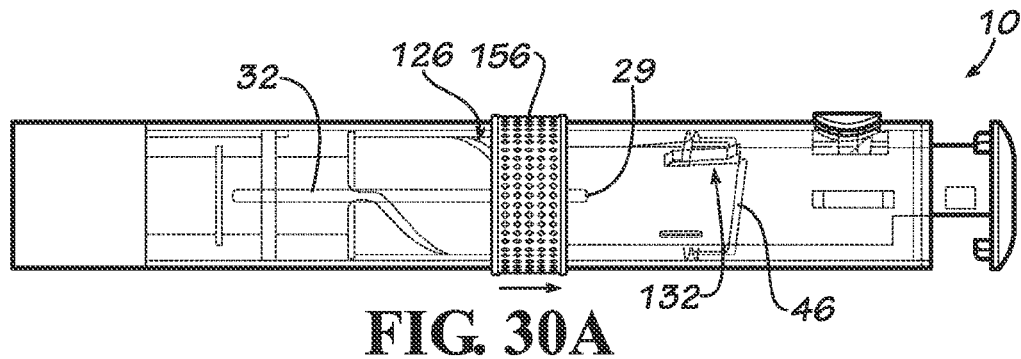
FIGS. 30A-30C show the lancing device of FIGS. 27A-27C, respectively, with the advance/eject mechanism in a fourth position with angular-contact elements rotated to rotate the forward-most lancing element and thereby sever its breakaway connections to the second-most-forward lancing element.
Figure 30B:
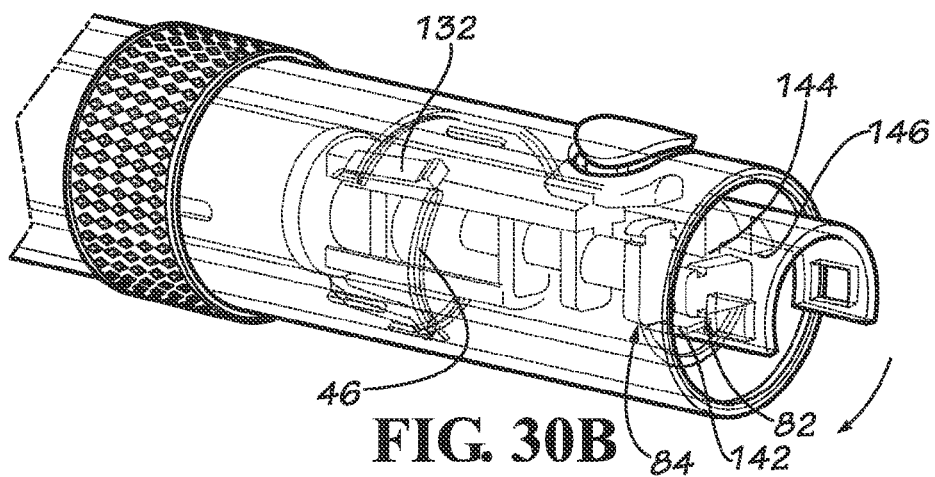
Figure 30C:
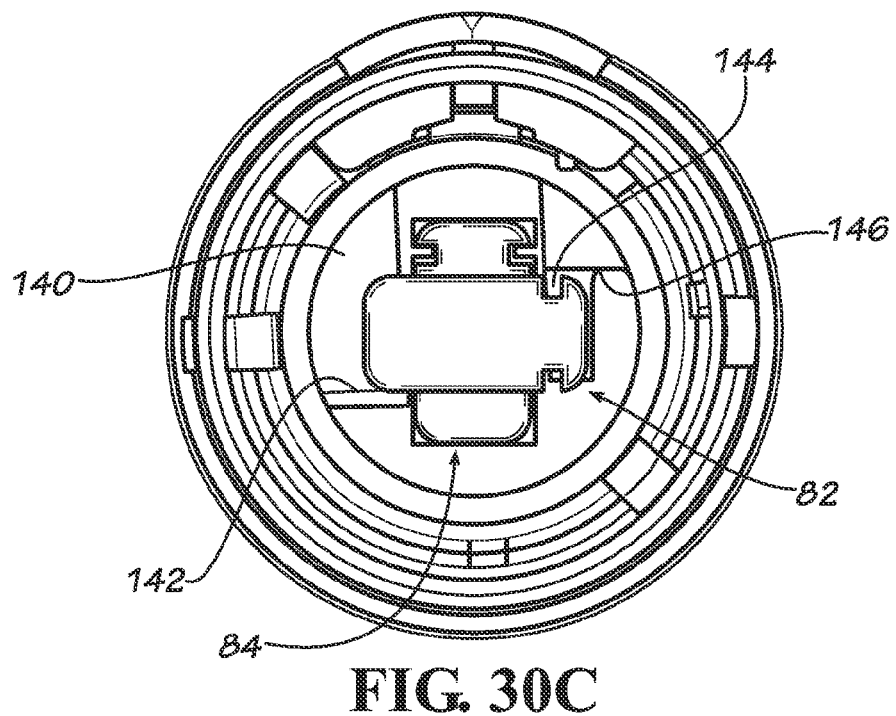
Figure 31A:
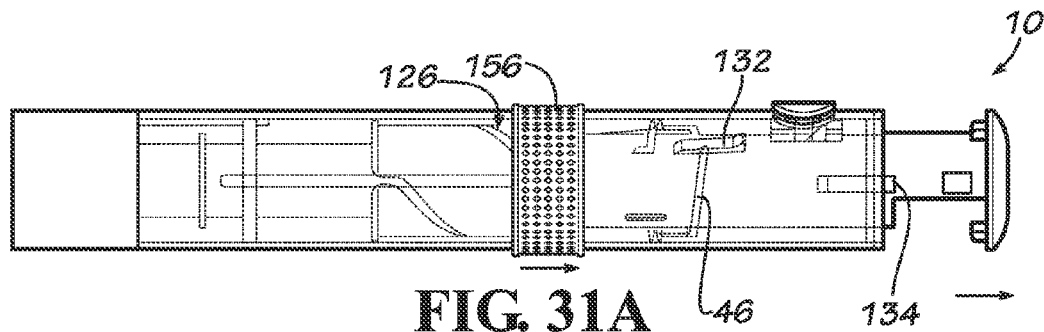
FIGS. 31A-31C show the lancing device of FIGS. 27A-27C, respectively, with the advance/eject mechanism in a fifth position with the axial-contact elements advanced to advance the severed forward-most lancing element.
Figure 31B:
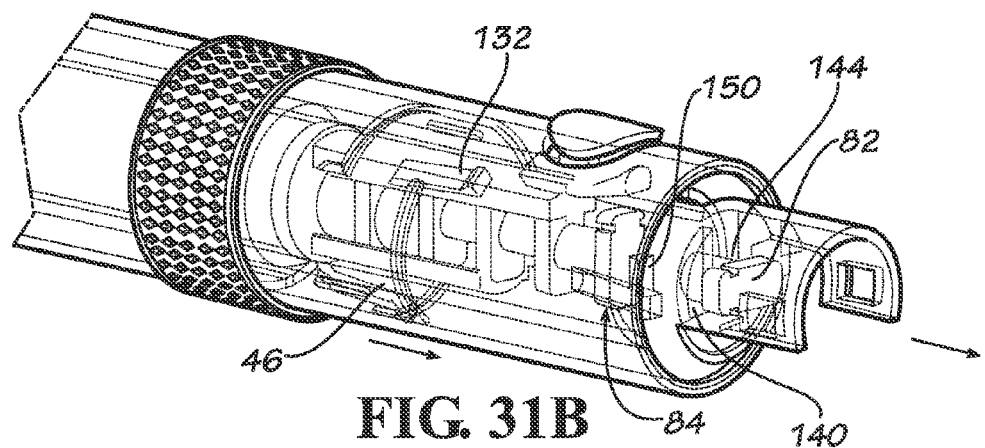
Figure 31C:
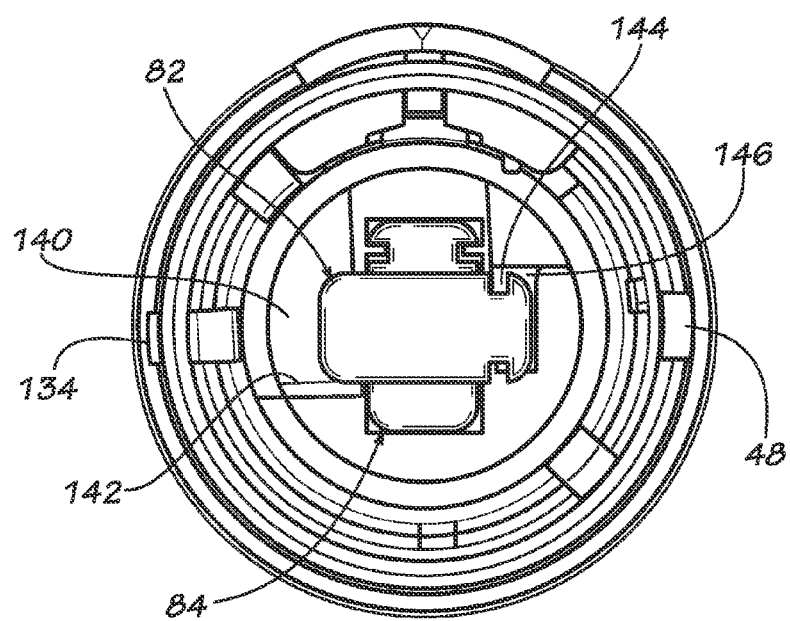

The axial contact members 140, 144, and 150 extend into the positioner bore 114 such that they do not interfere with free axial translation of the multi-lancet chain 80 (or the lancet holder 50 movably carrying it) when the positioning member 110 is in a first angular position (see FIGS. 27A-C). But when the positioning member 110 is rotated to a second angular position (see FIGS. 28A-C), the axial contact members 140, 144, and 150 now interfere with axial translation of the lancet holder 50. In operation, actuating the actuator 156 causes rotational and axial movement of the positioning member 110, which causes the axial contact members 140, 144, and 150 and the angular contact walls 142 and 146 to engage the multi-lancet chain 80 (lancets 84 and caps 82) for the advancement and ejection thereof, as described below.

In addition, the positioner body 112 includes a catch-element opening 152 that permits the spring-biased lancet-holder catch element (e.g., the depicted cantilever finger) 70 to extend outward through the positioner body so it is out of the way of the multi-lancet chain 80 during lancet advancement and ejection and also so it can engage the housing catch element (e.g., the depicted release opening) 31 to releasably retain the lancet holder in the charged position. In the depicted embodiment, for example, the catch-element opening 152 of the positioner body 112 is slotted and includes a first-stage rotational (e.g., circumferential) segment, a second-stage axial segment, a third-stage rotational segment, and a fourth-stage axial segment with a relief-opening portion 152a, with these segments sequentially arranged and interconnected. These segments of the positioner-body opening 152 correspond to the motion stages of the positioner 110, with the relief-opening portion 152a being where the lancet-holder catch element 70 extends through to engage the housing catch element 31 in the charged position. The slotted opening 152 is typically positioned adjacent the axial and angular contact members 140, 144, 150, 142, and 146 of the positioner 110.

Furthermore, the positioner body 112 includes an ejection opening portion 153 between the first-stage rotational segment of its slotted opening 152 and its front end 116 through which the lancing elements 81 can be ejected. The ejection opening portion 153 can be in communication with the opening 152 for ease of manufacture.

Figure 21:
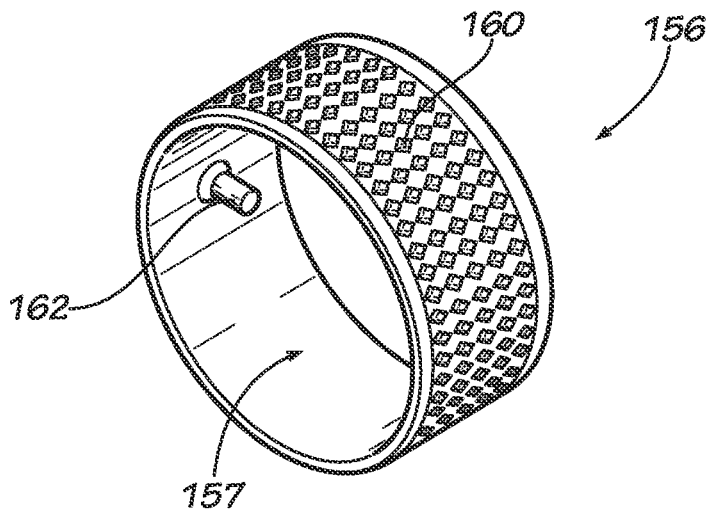
FIG. 21 shows an actuator of the lancing device of FIG. 3.
Figure 22:
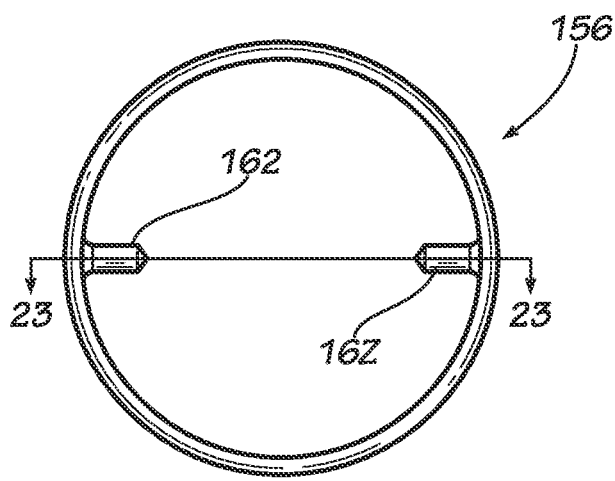
FIG. 22 is a front end view of the actuator of FIG. 21.
Figure 23:
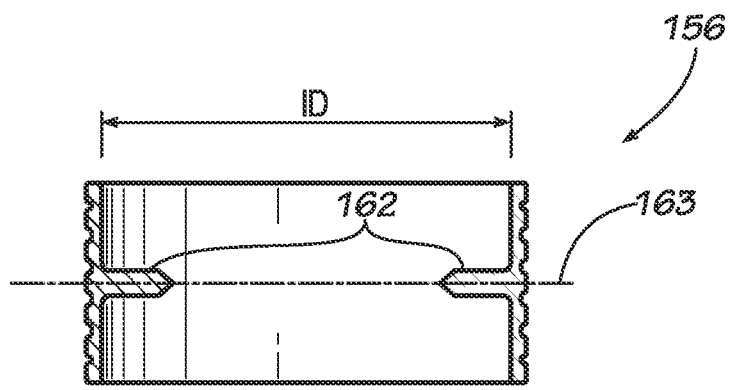
FIG. 23 is a cross sectional view of the actuator of FIG. 21 taken at line 23-23.

FIGS. 21-23 show the actuator 156 in greater detail. As described above, the actuator 156 is movably mounted to the housing 20 and configured such that its forward operating movement causes rotational and axial movement of the positioning member 110 to advance the multi-lancet chain 80 forward and eject the most forward lancing element 81. As depicted, the actuator 156 includes a cylindrical or ring-shaped collar with a bore 157 defined axially therethrough and with the control pins 162 extending inwardly therefrom. The actuator collar 156 has an internal diameter (ID) that defines its bore 157 and is substantially similar to (e.g., slightly larger than) the outer diameter of the housing 20. The control pins 162 are typically positioned generally opposite each other and thus define and extend along a diameter line 163. The pins 162 are sized and shaped to freely move within the control slots 32 of the housing 20 and the helical control channels 126 of the positioning member 110. The actuator control pins 162 can be provided by any structures that protrude from the actuator 156 and extend through the housing control slots 32 into engagement with the positioner control channels, for example bars, rods, tabs, plates, or other protrusions. And the actuator 156 can be provided by any structure that is mountable onto the housing 20 for movement to drive the positioner 110 through its operating and return motions as described herein, such as a semi-circular handle, two unconnected finger pads (with the control pins including retainer holding them in the control channel), or other conventional actuating structures. Optionally, a knurled surface 160 can be provided on the outer periphery of the collar to provide for easily grasping and moving it axially along the housing 20.

Figure 24:
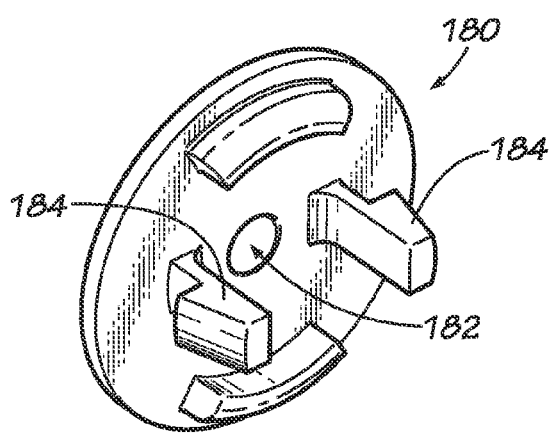
FIG. 24 is a rear perspective view of a housing front endcap of the lancing device of FIG. 3.
Figure 25:
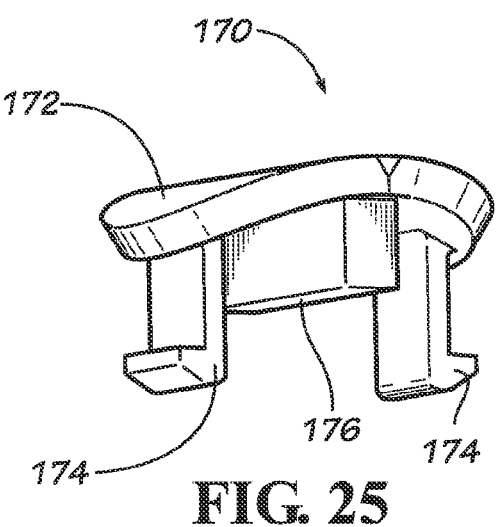
FIG. 25 is a perspective view of a release button of the lancing device of FIG. 3.
Figure 26:
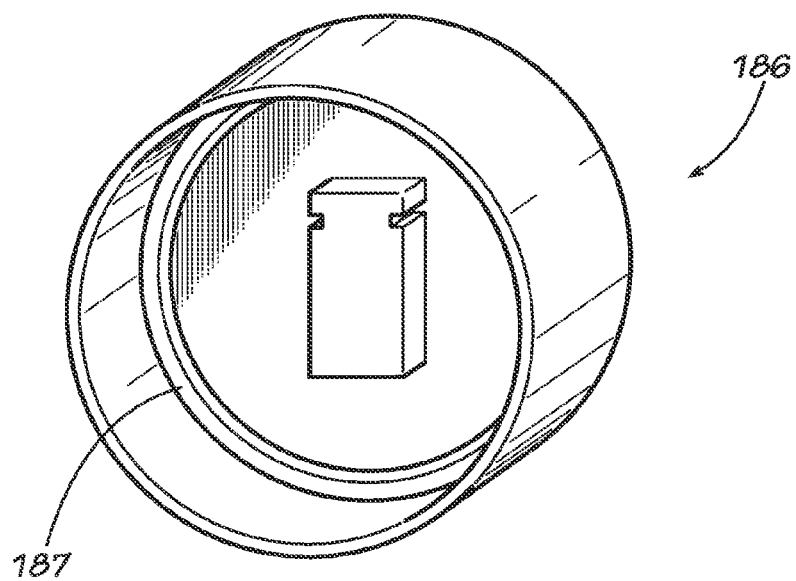
FIG. 26 is a perspective view of a housing rear endcap of the lancing device of FIG. 3.

FIGS. 24-26 show greater detail of other components of the lancing device 10, particularly the release button 170, the front endcap 180, and the rear endcap 186. Referring to FIG. 24, the front endcap 180 includes an endwall having a lancing opening 182 defined therethrough and one or more (e.g., the two depicted) attachments 184. As shown, the endwall can be in the form of a disc-shaped body that generally conforms to the shape of the housing body 12 and closes off its rear end. The lancing opening 182 receives the sharp tip section 102 of the lancet needle 100 therethrough to prick the subject at the lancing site. And the attachments 184 fix the front endcap 180 to the positioning member 110 so that the endcap moves (translates and rotates) with the positioning member. For example, the attachments 184 can be provided by fingers that extend rearward from the body and insert into apertures 154 in the positioning member 110 (see FIG. 18).

FIG. 25 shows the release button 170 in greater detail. As depicted, the release button includes a manipulation body (e.g., a finger pad) 172 with one or more (e.g., the two depicted) slideable retainers 174 and the releasing element 176 extending therefrom. The slideable retainers 174 can be provided by fingers that slidingly engage the release opening 31 of the housing 20 and retain the release button 170 to the housing. And the releasing element 176 extends into the housing 20 through the release opening 31 and into contact with the catch element (e.g., cantilever) 70 of the lancet holder 50 when the manipulation body 172 is pressed. This pressing contact releases the lancet-holder catch cantilever 70 from engagement with the housing 20, thereby freeing the lancet holder 50 to move through the lancing stoke, from its retracted position to its extended position with the sharp tip 102 of the lancet 84 extending through the lancing opening 182 of the front endcap 180.

FIG. 26 shows the rear endcap 186 in greater detail. In the depicted embodiment, the rear endcap 186 includes an endwall and a peripheral sidewall extending therefrom and defining a bore. The endwall can be in the form of a disc-shaped body that generally conforms to the shape of the housing body 12 and closes off its rear end, and the sidewall can be generally cyindrical. The rear endcap 186 mounts to the rear end 27 of the housing 20 and is typically provided to retain the drive spring 190 in the housing 20 between/against the drive flange 62 of the lancet holder 50. In one form, a rib 187 projects from the sidewall into the bore to provide for engagement with a channel 35 that is formed around the periphery of the housing body 22 near the second end 27 to snap-fit the two parts together (see FIG. 4).

In another aspect, the invention relates to advance-and-eject mechanisms, such as those described herein, for inclusion in lancing devices, such as those described herein or others. It will be noted that the advance-and-eject mechanism can be incorporated into other lancing device than those specifically described herein. For example, in one embodiment the advance-and-eject mechanism is incorporated into a lancing device including a non-reuse mechanism that prevents re-use of the lancets, the multi-lancet chain includes only lancets (without caps), and the advance-and-eject mechanism operates to advance and eject lancets but not caps.

FIGS. 27A-32C show the operation of the advance/eject mechanism 111 of the depicted embodiment, and as such also illustrate a method of advancing and ejecting lancets according to another aspect of the invention. First a fresh multi-lancet chain 80 is loaded into the lancing device 10 by being positioned in the lancet holder 50 with a use (first or forward-most) lancing element 81 (in this case a cap 82) in the use position engaged by the retention detents 74 of the lancet holder (see FIG. 15). The use-positioned lancing element 81 can be advanced into the use position by operation of the advance/eject mechanism 111, as will become apparent from the following description of its method of use.

As shown in FIGS. 27A-C, the advance/eject mechanism 111 is in a ready or first position, with the positioning member 110 in the first position, which defines a first angular position and a first axial position of the positioning member and the most-forward lancing element. In the first angular position, the axial-contact walls 140, 144, and 150 of the positioning member 110 are positioned clear of the lancing stroke pathway so that the lancet holder 50 (and the multi-lancet chain 80 movably mounted thereto) can move axially therethrough. And in the first angular position, the motion-restricting cam followers 132 are movably engaged with the beginning of the first-stage translation-restricting segment 42 of the motion-restricting cams 40.

To begin the advancement and ejection operation on the multi-lancet chain 80, the actuator 156 is moved axially forward (see the linear directional arrow of FIG. 28A) through a first segment of its forward operational motion. As the actuator 156 moves axially forward, as controlled by the control slots 32 in the housing 20, the actuator control pins 162 slide forward in the helical control channels 126 of the positioning member 110, but the motion-restricting cam followers 132 of the positioning member 110 are guided along the first-stage translation-restricting segment 42 of the motion-restricting cams 40, causing the positioning member to rotate (see the rotational direction arrow of FIG. 28B) in a first angular direction (e.g., clockwise). In the depicted embodiment, for example, the positioning member 110 rotates about 90 degrees from the first to the second position (from the first angular position to the second angular position). When the motion-restricting cam followers 132 of the positioning member 110 reach the end of the first-stage translation-restricting segment 42 of the motion-restricting cams 40, the positioning member 110 has been rotated to a second position (see FIGS. 28A-28C), which defines a second angular position of the positioning member and the most-forward lancing element. As can be seen, the positioning member 110 has also moved forward slightly due to the slightly helical configuration of the generally circumferential first-stage translation-restricting segment 42.

In the second angular position, the axial-contact members 140, 144, and 150 have been rotated into the lancing stroke path where they interfere with axial travel of the multi-lancet chain 80. The two forward axial-contact members 140 and 144 extend behind the flange 90 of the forward-most lancing element 81 (cap 82) (see FIG. 28C) and the rear axial-contact member 150 extends behind the flange of the second-most-forward lancing element. Once the positioning member 110 has advanced to the second position, the motion-restricting cam followers 132 of the positioning member 110 are no longer receiving guidance from the first-stage translation-restricting segment 42 of the motion-restricting cams 40.

Then the actuator 156 is moved further axially forward (see the linear directional arrow of FIG. 29A) through a second segment of its forward operational motion. As the actuator 156 continues moving forward, as controlled by the control slots 32 in the housing 20, the actuator control pins 162 slide further forward in the helical control channels 126 of the positioning member 110, but the motion-restricting cam followers 132 of the positioning member 110 are now guided along the second-stage rotation-restricting segment 44 of the motion-restricting cams 40, causing the positioning member to translate forward (see the linear directional arrow of FIGS. 29A-29B). As the positioning member 110 is moved axially forward, the axial-control members 140, 144, and 150 engage and push forward the flanges 90 of the two most-forward lancing elements 81 (cap 82 and lancet 84) to advance the multi-lancet chain 80 forward. This causes the flange 90 of the second-most-forward lancing element 81 (lancet 84) to be disengaged from the retention detents 74 and the third-most-forward lancing element to become removably engaged with the retention detents (see FIG. 29B). As such, the two most-forward lancing elements 81 now extend forward beyond the retention detents 74 and the front end of the angular-positioning jaw members 71. The breakaway connections 94 are strong enough to ensure the lancing elements 81 remain interconnected when axial movement of the positioning member 110 causes the axial-control members 140, 144, and 150 to advance the multi-lancet chain 80 forward.

When the motion-restricting cam followers 132 of the positioning member 110 reach the end of the second-stage rotation-restricting segment 44 of the motion-restricting cams 40, the positioning member 110 has been translated to a third position (see FIGS. 29A-29C), which defines a second axial position of the positioning member and the most-forward lancing element. In the third position, the motion-restricting cam followers 132 of the positioning member 110 are no longer receiving guidance from the second-stage rotation-restricting segment 44 of the motion-restricting cams 40.

Then the actuator 156 is moved further axially forward (see the linear directional arrow of FIG. 30A) through a third segment of its forward operational motion. As the actuator 156 moves further axially forward, as controlled by the control slots 32 in the housing 20, the actuator control pins 162 slide further forward in the helical control channels 126 of the positioning member 110, but the motion-restricting cam followers 132 of the positioning member 110 are guided along the third-stage translation-restricting segment 46 of the motion-restricting cams 40, causing the positioning member to rotate further (see the rotational direction arrow of FIG. 30B) in the first angular direction. When the motion-restricting cam followers 132 of the positioning member 110 reach the end of the third-stage translation-restricting segment 46 of the motion-restricting cams 40, the positioning member 110 is rotated to a fourth position (see FIGS. 30A-30C), which defines a third angular position of the positioning member and the most-forward lancing element.

As the positioning member 110 is rotated from the third position to the fourth position, the angular-contact members 142 and 146 engage the flange 90 of the forward-most lancing element 81 (cap 82) and rotationally drive it to a conforming angular position as the positioning member 110. This rotation of the forward-most lancing element (cap 82) relative to the second-most-forward lancing element (lancet 84) generates torsional forces that cause mechanical failure of the breakaway connections 94 between the forward-most lancing element and the second-most-forward lancing element. In the depicted embodiment, the positioning member 110 rotates about 90 degrees from the second to the third position (from the second angular position to the third angular position), which causes the forward-most lancing element (cap 82) to rotate about 90 degrees relative to the second-most-forward lancing element (lancet 84). So the forward-most lancing element (cap 82) has now been mechanically detached from the second-most-forward lancing element (lancet 84), but the forward-most cap remains in place because it is still supported on the needle tip 102 of the second-most-forward lancet.

With the forward-most lancing element (cap 82) rotated relative to the second-most-forward lancing element (lancet 84), the positioner's forward axial-contact members 140 and 144 remain positioned behind the flange 90 of the forward-most cap, while the positioner's rear axial-contact member 150 remains positioned not to interfere with the flange 90 of the second-most-forward lancet. Also, the motion-restricting cam followers 132 of the positioning member 110 are now positioned beyond the end of the third-stage translation-restricting segment 46 of the motion-restricting cams 40, so they are no longer providing any motion guidance by restricting rotation or translation. And the control pins 162 of the actuator 156 are now positioned at the forward end 127 of the helical control channels 126 of the positioning member.

Because of all of this, further forward axial movement of the actuator 156 (see the directional arrows of FIGS. 31A-31B) through a fourth segment of its forward operational motion causes the actuator control pins 162 to push axially on the forward end 127 of the helical control channels 126 of the positioning member 110, without any guidance or restriction on the motion of the positioning member. As a result, the positioning member 110 now translates further axially forward to a fifth position (see FIGS. 31A-31C), which defines a third axial position of the positioning member and the most-forward lancing element. In the fifth position, further forward motion of the actuator 156 is stopped by the actuator control pins 162 contacting the forward-most ends 29 of the housing control slots 32. And further forward motion of the positioning member 110 is stopped by its relief opening portion 152a receiving (and thus being restrained from further forward movement) by the cantilever catch finger 70 of the lancet holder 50.

In the fifth position, the forward-most lancing element (cap 82) has now been mechanically detached from the second-most-forward lancing element (lancet 84), then advanced forward without the second-most-forward lancet also being advanced. So the forward-most cap 82 has now been advanced beyond the needle tip 102 of the secondmost-forward lancet 84, and is not supported in place by anything. And the ejection opening 153 of the positioning member 110 has been rotated to directly below the separated and freed forward-most cap 82, and the front endcap 180 has been advanced forward with the positioning member. So by the force of gravity the forward-most cap 82 now falls out of the lancing device 10 through the ejection opening 153 of the positioning member 110 and is thereby ejected for discarding. At this point, the forward-most lancing element is now a fresh lancet 84 in the use position ready for lancing use (see FIGS. 32A-32C).

Figure 32A:
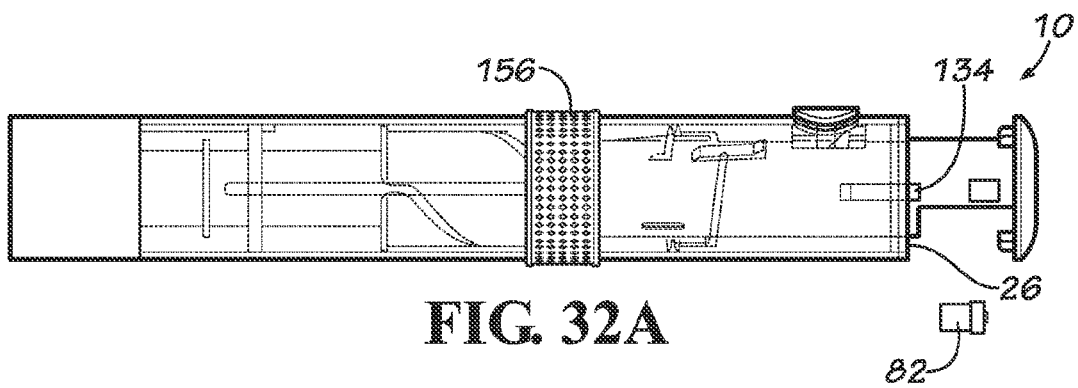
FIGS. 32A-32C show the lancing device of FIGS. 27A-27C, respectively, with the advance/eject mechanism in the fifth position with the forward-most lancing element being ejected by gravity.
Figure 32B:
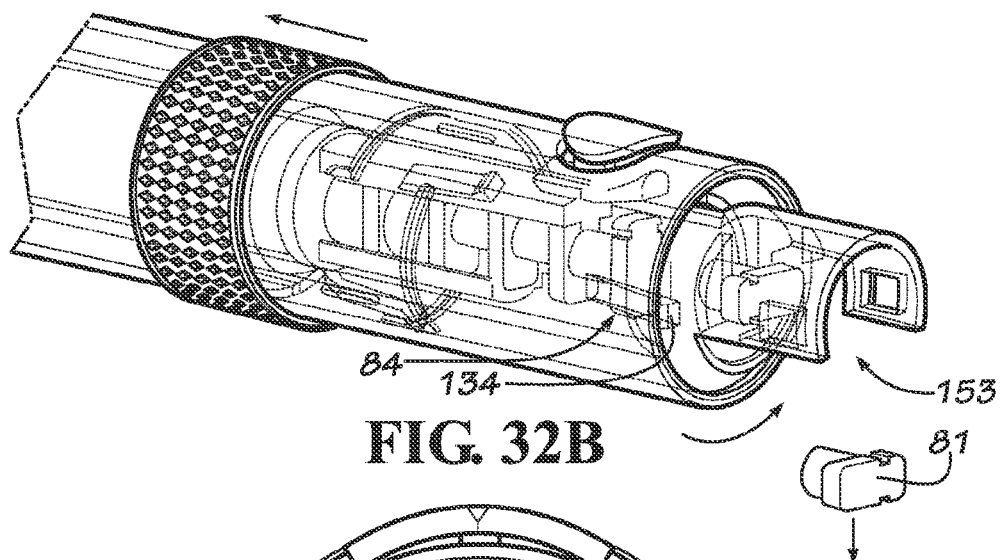
Figure 32C:
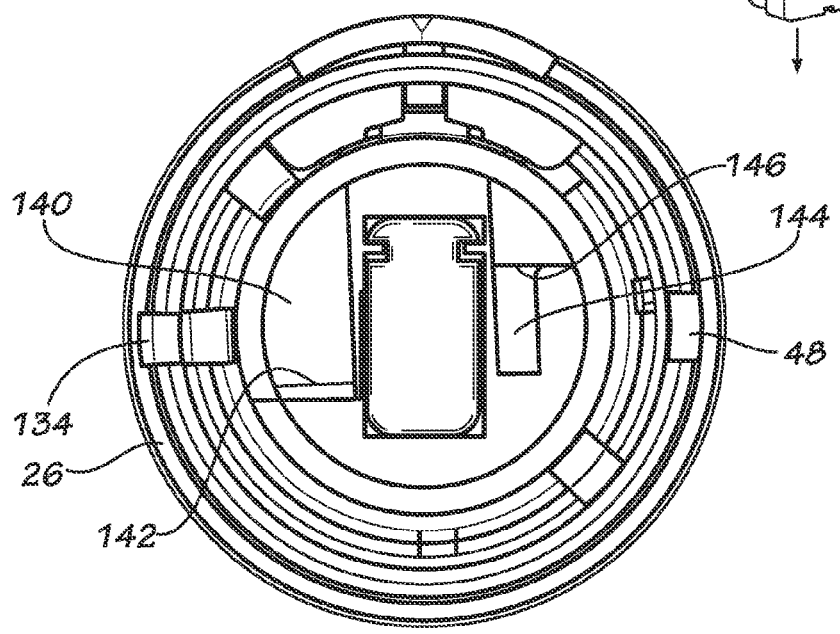

In addition, in the fifth position the motion-restricting retraction element (e.g., cantilever) 134 of the positioning member 110 is now engaged with the axial-motion-restricting element (e.g., a lip or edge of the first end 26) of the housing 20 (see FIGS. 32A-32C). After ejecting the forward-most lancing element, the actuator 156 is then retracted through a rearward return stroke to the ready/first position of FIGS. 27A-27C. As the actuator 156 is retracted (see the linear directional arrow of FIG. 32B), its control pins 162 movably engaged with the positioner helical control channels 126 cause rotation of the positioning member 110 in a second angular direction (e.g., counter-clockwise) that is opposite/reverse relative to the first angular direction (see rotational direction arrow of FIG. 32B). This causes reverse rotation of the positioning member 110 from the third angular position to the first angular position, which in turn causes the retraction cantilever 134 to rotate around/along the first end 26 of the housing 20 during a first stage of a rearward return motion of the actuator 156. Upon the first angular position being reached, for example after about 180 degrees of reverse rotation, the retraction cantilever 134 reaches the axial-motion-permitting element, for example the depicted ramp 48 that is formed in the first end 26 of the housing 20. The ramp 48 allows the retraction cantilever 134 to deflect inward and disengage from the housing first end 26, which allows the positioning member 110 to move axially within the housing 20 back to its ready/first position during a second stage of a rearward return motion of the actuator 156.

Once the actuator 156 is back to the ready/first position, the lancing procedure may begin by charging the drive mechanism (e.g., via further retraction of the actuator 156 toward the rear end 33 of the control slot 32, or otherwise), and then releasing the lancet holder 50 (e.g., via depressing the release button 170) to propel the lancet holder (and the forward-most lancet 82 carried by it) from the charged position within the housing to the advanced/extended position. In the advanced/extended position, the sharp tip 102 of the lancet needle 100 projects through the opening 182 of the front endcap 180 to prick the subject at the lancing site. The lancet 84 is then retracted back to within the housing 20 by the return spring 192.

After pricking the subject, the used lancet 82 is advanced and ejected by repeating the process of operating the advance/eject mechanism 111, except this time the forward-most lancing element in the use position is the used lancet instead of its cap 84. Upon concluding the advance/eject process again, the forward-most lancing element in the use position is now a cap of a fresh lancet. The lancing device can now be safely set aside until it is needed again, at which time the advance/eject mechanism 111 can be operated again as needed for lancing use.

While the invention has been described with reference to preferred and example embodiments, it will be understood by those skilled in the art that a variety of modifications, additions and deletions are within the scope of the invention, as defined by the following claims.

What is claimed is:

1. A lancing device for use with a multi-lancet chain to lance skin, the multi-lancet chain including a series of lancing elements interconnected by breakaway connections, the lancing device comprising:
   a housing;
   a lancet holder that is received in the housing and carries the multi-lancet chain, wherein a forward-most lancing element of the multi-lancet chain is carried by the lancet holder through a lancing stroke to an extended position relative to the housing for lancing the skin;
   an advance-and-eject mechanism including a positioning member that is received in the housing, carries the lancet holder carrying the multi-lancet chain, and is operable to advance and eject the forward-most lancing element of the multi-lancet chain, wherein the advance-and-eject mechanism further includes an actuator, one or more control channels, a cam-and-follower mechanism, one or more axial-contact members, and one or more angular-contact members, wherein actuating the actuator relative to the one or more control channels imparts rotational and axial forces on the positioning member, wherein the cam-and-follower mechanism selectively restricts rotational and axial motion of the positioning member to induce first-stage rotation, second-stage translation, and third-stage rotation, wherein the first-stage rotation rotates the one or more axial-contact members from a non-interference position to an interference position relative to the forward-most lancing element resulting in an interfered-with forward-most lancing element, the second-stage translation advances the one or more axial-contact members and the interfered-with forward-most lancing element, and the third-stage rotation rotates the one or more angular-contact members and the forward-most lancing element to sever its breakaway connection to the multi-lancet chain to eject the forward-most lancing element from the lancing device.

2. The lancing device of claim 1, wherein the actuator includes one or more control pins and the control channels are formed in the positioning member and receive the control pins to impart the rotational and axial forces on the positioning member.

3. The lancing device of claim 2, further comprising one or more control slots formed in the housing and through which the control pins extend, wherein the housing control slots are generally linear and the positioning-member control channels are generally helical.

4. The lancing device of claim 1, wherein the cam-and-follower mechanism is formed by cooperating portions of the housing and the positioning member and includes one or more cams and one or more cam followers that contact and are guided by the cams as the actuator is actuated.

5. The lancing device of claim 4, wherein the cams each include a first-stage segment that restricts translation of the positioning member as the respective cam follower tracks along it, a second-stage segment that restricts rotation of the positioning member as the respective cam follower tracks along it, a third-stage segment that restricts translation of the positioning member as the respective cam follower tracks along it.

6. The lancing device of claim 5, wherein the positioning member rotates a first about 90 degrees from a first angular position to a second angular position during the first-stage rotation, and the positioning member rotates a second about 90 degrees from the second angular position to a third angular position during the third-stage rotation.

7. The lancing device of claim 5, wherein the first-stage cam segment is generally circumferentially arranged, the second-stage cam segment is generally axially arranged, and the third-stage segment cam segment is generally circumferentially arranged.

8. The lancing device of claim 1, wherein further actuating the actuator relative to the control channels imparts an axial force on the positioning member that induces fourth-stage translation that advances the axial-contact members and the forward-most lancing element to a position clear of the multi-lancet chain to eject it from the lancing device.

9. The lancing device of claim 8, wherein the third-stage rotation rotates the axial-contact members into a second interference position where they interfere with the forward-most lancing element during the fourth-stage translation.

10. The lancing device of claim 1, wherein the positioning member defines a bore that receives the lancet holder and multi-lancet chain, and wherein the axial-contact members and the angular-contact members of the positioning member extend into the positioning member bore in the non-interference position clear of the forward-most lancing element and in the interference position interfering with the forward-most lancing element.

11. The lancing device of claim 1, wherein the axial-contact members face generally axially forward and the angular-contact members face generally transversly.

12. The lancing device of claim 1, wherein the axial-contact members that engage the forward-most lancing element are positioned forward of a rear axial-contact member that engages a second-most-forward one of the lancing elements of the multi-lancet chain.

13. The lancing device of claim 1, wherein the positioning member further includes a translation-restricting retraction member that engages a cooperating translation-restricting element of the housing to induce the positioning member to rotate when the actuator is returned through a first stage of a return stroke.

14. The lancing device of claim 13, wherein the housing includes a translation-permitting element that enables the positioning member to translate when the actuator is returned through a second stage of the return stroke.

15. The lancing device of claim 1, wherein the housing includes a front endcap that is attached to and moves with the positioning member so that the front endcap translates with the endcap to provide clearance for ejecting the forward-most lancing element from the housing.

16. A lancing device for use with a multi-lancet chain to lance skin, the multi-lancet chain including a series of lancing elements interconnected by breakaway connections, the lancing device comprising:
a housing;
a lancet holder that is received in the housing and carries the multi-lancet chain, wherein a forward-most lancing element of the multi-lancet chain is carried by the lancet holder through a lancing stroke to an extended position relative to the housing for lancing the skin;
an advance-and-eject mechanism including a positioning member that is received in the housing, carries the lancet holder carrying the multi-lancet chain, and is operable to advance and eject the forward-most lancing element of the multi-lancet chain, wherein the advance-and-eject mechanism further includes an actuator, one or more control channels, a cam-and-follower mechanism, one or more axial-contact members, and one or more angular-contact members, wherein actuating the actuator relative to the control channels imparts rotational and axial forces on the positioning member, wherein the cam-and-follower mechanism includes one or more cams formed on the housing and one or more cam followers formed on the positioning member that contact and are guided by the one or more cams as the actuator is actuated to selectively restrict rotational and axial motion of the positioning member to induce first-stage rotation, second-stage translation, and third-stage rotation, wherein the one or more cams each include a first-stage segment that is generally circumferentially arranged and that restricts translation of the positioning member as the respective cam follower tracks along the positioning member to induce the first-stage rotation to rotate the one or more axial-contact members from a non-interference position to an interference position relative to the forward-most lancing element resulting in an interfered-with forward-most lancing element, a second-stage segment that is generally axially arranged and that restricts rotation of the positioning member as the respective cam follower tracks along the positioning member to induce the second-stage translation to advance the one or more axial-contact members and the interfered-with forward-most lancing element, and a third-stage segment that is generally circumferentially arranged and that restricts translation of the positioning member as the respective cam follower tracks along the positioning member to induce the third-stage rotation to rotate the one or more angular-contact members and the forward-most lancing element to sever its breakaway connection to the multi-lancet chain to eject the forward-most lancing element from the lancing device.

17. The lancing device of claim 16, wherein the actuator includes one or more control pins and the control channels are formed in the positioning member and receive the control pins to impart the rotational and axial forces on the positioning member, and further comprising one or more control slots formed in the housing and through which the control pins extend, wherein the housing control slots are generally linear and the positioning-member control channels are generally helical.

18. The lancing device of claim 16, wherein further actuating the actuator relative to the control channels imparts an axial force on the positioning member that induces fourth-stage translation that advances the axial-contact members and the forward-most lancing element to a position clear of the multi-lancet chain to eject it from the lancing device.

19. The lancing device of claim 1, wherein the positioning member defines a bore that receives the lancet holder and multi-lancet chain, wherein the axial-contact members and the angular-contact members of the positioning member extend into the positioning member bore in the non-interference position clear of the forward-most lancing element and in the interference position interfering with the forward-most lancing element, wherein the axial-contact members face generally axially forward and the angular-contact members face generally transversly, and wherein the axial-contact members that engage the forward-most lancing element are positioned forward of a rear axial-contact member that engages a second-most-forward one of the lancing elements of the multi-lancet chain.

20. A multi-lancet chain for use with a lancing device to lance skin, comprising:
a series of lancing elements in the form of lancets and caps; and breakaway connections extending between and interconnecting the lancets and the caps,
wherein the lancets each include a body, a flange, and a needle extending through the body and the flange, wherein the needle includes a sharp tip extending from a front of the lancet and a rear-connecting portion extending from a rear of the lancet,
wherein the caps each include a body and a flange, wherein a rear of the cap receives the needle tip of a trailing one of the lancets and a front of the cap receives the rear-connecting portion of the needle of a preceding one of the lancets,
wherein the flanges of the lancets and the flanges of the caps have generally the same shape, and
wherein the flanges of the lancets and the flanges of the caps include grooves that receive guide elements of the lancing device.

\* \* \* \* \*